(12) United States Patent
Suetsugu et al.

(10) Patent No.: US 6,676,932 B2
(45) Date of Patent: Jan. 13, 2004

(54) ULTRAVIOLET ABSORBENT, PHOTOSTABILIZER, ULTRAVIOLET RAY-ABSORBING COMPOSITION, PHOTOSTABILIZED COMPOSITION AND EXTERNAL PREPARATION FOR SKIN

(75) Inventors: Masaru Suetsugu, Yokohama (JP); Eijiro Hara, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 50 days.

(21) Appl. No.: 10/167,423

(22) Filed: Jun. 13, 2002

(65) Prior Publication Data

US 2003/0198608 A1 Oct. 23, 2003

(30) Foreign Application Priority Data

Jun. 15, 2001 (JP) .......................... 2001-182640

(51) Int. Cl.[7] .............. A61K 7/42; A61K 7/44; A61K 7/00; A61K 31/50
(52) U.S. Cl. .............. 424/59; 424/60; 424/400; 424/401; 514/252.03
(58) Field of Search .............. 424/59, 60, 400, 424/401; 514/252.03

(56) References Cited

U.S. PATENT DOCUMENTS

| 4,396,735 A | 8/1983 | Minagawa et al. |
| 6,395,896 B2 | 5/2002 | Suetsugu et al. |

FOREIGN PATENT DOCUMENTS

| EP | 1 108 712 A1 | 6/2001 |

OTHER PUBLICATIONS

Bellasio, E. et al., "Sintesi Di 3–Idrazinopiridazine con Sostituenti Basici in Posizione 6, Dotate di Attivita' Ipotensiva," *Il Farmaco Edizione Scientifica*, Nov. 1969, vol. 24, No. 11, pp. 919–929, XP001108906.

Farina, F. et al., Abstract, An. Quim Ser. C, RN 82226–35–5, 82226–41–3, 1981, vol. 77, No. 2, Chemical Abstracts Service, Columbus OH, Database accession no. 97:23722/DN, HCAPLUS, XP002216726.

Kaju, K. et al., Abstract, Gifu Yakka Daigaku Kiyo, RN 21131–05–5, 21131–06–6, 1967, NO. 17, Chemical Abstracts Service, Columbus OH, Database accession no. 70:28883/DN, HCAPLUS XP002216727.

Omori, S. et al., Abstract, Kami Pa Gikyoshi, RN 123–33–1, 1993, vol. 47, No. 11, Chemical Abstracts Service, Columbus OH, Database accession no. 121:182180/DN, HCAPLUS XP002216728.

Kwon, S. et al., Abstract, Yakhak Hoechi, 2000, vol. 44, No. 1, Chemcial Abstracts Service, Columbus OH, Database accession o. 133:2062/Dn, HCAPLUS XP002216729.

A. Bistrzycki and H. Simonis, "Synthese von Pyridazonderivaten," *Chemische Berichte*, 1899, pp. 534–536, Germany.

*Primary Examiner*—Shelley A. Dodson
(74) *Attorney, Agent, or Firm*—Snider & Associates; Ronald R. Snider

(57) ABSTRACT

Providing an ultraviolet absorbent or photostabilizer with excellent absorption over a wide ultraviolet wavelength range and great stability and a high safety profile, as well as an ultraviolet-absorbing composition, a photostabilized composition and an external preparation for skin, where the pyridazine derivative of the following general formula and/or a salt thereof is included as the effective component of the ultraviolet absorbent or photostabilizer, or is included in the ultraviolet-absorbing composition, the photostabilized composition and the external preparation for skin:

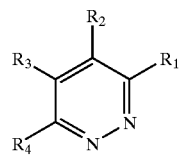

Wherein $R_1$, $R_2$, $R_3$ and $R_4$ are not simultaneously hydrogen atom; and $R_2$ and $R_3$ are not simultaneously morpholino group.

29 Claims, 9 Drawing Sheets

ULTRAVIOLET ABSORBENT, PHOTOSTABILIZER, ULTRAVIOLET RAY-ABSORBING COMPOSITION, PHOTOSTABILIZED COMPOSITION AND EXTERNAL PREPARATION FOR SKIN

This application claims the priority of Japanese Patent application No.2001-182640 filed on Jun. 15, 2001, which is incorporated herein by reference.

BACKGROUND OF THE INVENTION

1. Field of the Invention

The present invention relates to an ultraviolet absorbent, a photostabilizer, and an ultraviolet ray-absorbing composition, a photostabilized composition and an external preparation for skin, which includes with an ultraviolet absorbent or a photostabilizer. Particularly, the invention relates to the improvement of the stability thereof and the use thereof.

2. Background Art

Among ultraviolet sunlight, ultraviolet ray of a wavelength below 290 nm is absorbed in the ozone layer, so such ultraviolet ray never reaches the ground surface. Ultraviolet ray of 290 nm to 400 nm reaches the ground surface and give various influences. From the standpoint of dermatology, it has been known that ultraviolet ray of a medium wavelength of 290 nm to 320 nm triggers erythema, blistering, melanism activation and chromatosis. Because ultraviolet ray of a long wavelength of 320 nm to 400 nm has an instantaneous melanism action to darken skin immediately after its irradiation and the energy reaches dermis, additionally, it is said that the ultraviolet ray influences the elastic fibers in vascular walls and connective tissues. These actions of medium- to long-wave ultraviolet ray promote skin senility so that these are believed to be one of causes generating spots, freckles, and wrinkles and the like.

For skin protection against such ultraviolet ray, ultraviolet absorbents such as benzotriazole derivatives, benzophenone derivatives, salicylic acid derivatives, p-aminobenzoic acid derivatives, cinnamic acid derivatives and urocanic acid derivatives have been used.

These ultraviolet absorbents are also used as photostabilizers for pigments, perfume, drugs and the like which are used in medical supplies and cosmetics.

Further, ultraviolet absorbents have been used in fields other than the fields of medical supplies and cosmetics. For example, ultraviolet absorbents have been used to give ultraviolet ray prevention effect to various materials such as paints, dyes, pigments, various resins, synthetic rubber, latex, film, fiber and glass, by adding the ultraviolet absorbents to these materials or coating these materials with the ultraviolet absorbents. Hence, the resulting products or the films thereof or products coated with the films can be protected against ultraviolet ray. Thus, the ultraviolet absorbents can prevent ultraviolet deterioration and modification to maintain their qualities.

Preferably, ultraviolet absorbents can absorb the whole ultraviolet wavelength range of 290 nm to 400 nm. Importantly, ultraviolet absorbents should not have any skin irritation when included in external preparations for skin. Furthermore, importantly, ultraviolet absorbents should not be decomposed under daylight exposure.

However, the ultraviolet absorbents of the related art are not necessarily satisfactory from these views. Further, the ultraviolet absorbents of the related art eventually cause coloring or deposition when used in combination with inorganic powder-based ultraviolet shielding agents commonly used in external preparations for skin. Accordingly, a more satisfactory photostabilizer has been demanded.

Ultraviolet absorbents of the related art in fields other than the fields of medical supplies and cosmetics have been disadvantageous in that the ultraviolet absorbents sublime or vaporize under heating during sintering of film or during resin molding and in that the ultraviolet absorbents gradually vaporize over time even without heating, leading to the attenuation of the effect.

SUMMARY OF THE INVENTION

In such circumstances with the problems of the related art, the present invention has been attained. It is a purpose of the invention to provide an ultraviolet absorbent and a photostabilizer, both having excellent absorption over a wide range of ultraviolet wavelengths as well as great stabilities together with great safety. It is an additional purpose of the invention to provide an ultraviolet-absorbing composition and a photostabilized composition, in both of which is included the ultraviolet absorbent or the photostabilizer. It is a further purpose of the invention to provide an external preparation for skin, in which the ultraviolet absorbent or the photostabilizer is included.

So as to achieve the purposes, the inventors have made investigations. Consequently, the inventors have found that a certain type of pyridazine derivatives have such properties as described above that the pyridazine derivatives are great ultraviolet absorbents and photostabilizers. Thus, the invention has been achieved.

In other words, the ultraviolet absorbent and the photostabilizer of the invention contain as the effective ingredient the following pyridazine derivative with great absorption over a wide range of ultraviolet wavelengths and with great stability and safety and a salt thereof.

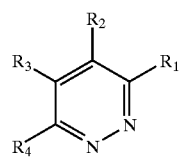

wherein $R_1$ and $R_4$ independently represent hydrogen atom, hydroxyl group, a lower alkyl group, a lower alkoxyl group or N $R_5$, $R_6$ group, wherein $R_5$ and $R_6$ may be the same or different and represent hydrogen atom, a lower alkyl group, or a lower hydroxyalkyl group; or $R_5$ and $R_6$ taken together with nitrogen atom represent a heterocyclic group selected from the group consisting of aziridinyl group, azetidinyl group, pyrrolidinyl group, piperidino group, hexahydroazepinyl group, heptamethylene imino group, octamethylene imino group, morpholino group, thiomorpholino group, piperazinyl group, and 4-lower alkylpiperazinyl group; $R_2$ and $R_3$ independently represent hydrogen atom, bromine atom, chlorine atom, hydroxyl group, a lower alkyl group, or a lower alkoxyl group or N $R_7$, $R_8$ group, wherein $R_7$ and $R_8$ may be the same or different and represent hydrogen atom, a lower alkyl group, or a lower hydroxyalkyl group; or $R_7$ and $R_8$ taken together with nitrogen atom represent a heterocyclic group selected from the group consisting of aziridinyl group, azetidinyl group, pyrrolidinyl group, piperidino group, hexahydroazepinyl group, heptamethylene imino group, octamethylene imino group, morpholino group, thiomorpholino group, piperazinyl group, and 4-lower alkylpiperazinyl group; wherein $R_1$, $R_2$, $R_3$ and $R_4$ are not simultaneously hydrogen atom and $R_2$ and $R_3$ are not simultaneously morpholino group.

The ultraviolet-absorbing composition of the invention characteristically includes the above-mentioned ultraviolet absorbent.

The photostabilized composition of the invention characteristically includes the above-mentioned ultraviolet absorbent.

The external preparation for skin in accordance with the invention characteristically includes the above-mentioned ultraviolet absorbent. Preferably, the external preparation for skin in accordance with the invention further includes an inorganic powder.

Additionally, the external preparation for skin in accordance with the invention includes the photostabilizer. Preferably, the external preparation for skin in accordance with the invention further includes sequestering agents.

Still additionally, the pyridazine derivative and/or a salt thereof is preferably included at 0.001 to 20 wt % in the external preparation for skin in accordance with the invention.

DETAILED DESCRIPTION OF THE INVENTION

Figure 1:
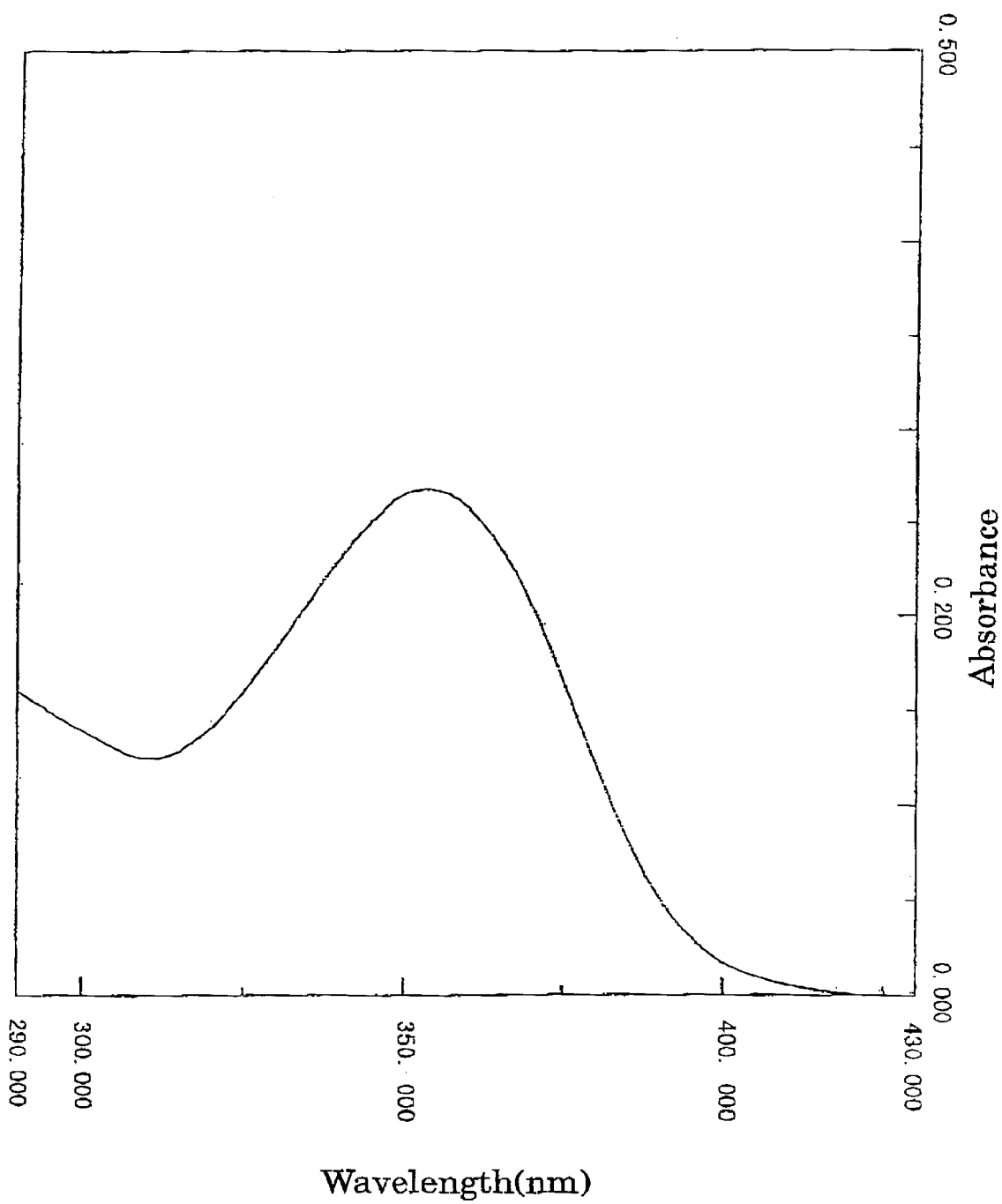
FIG. 1 is an ultraviolet absorption spectrum of the inventive pyridazine derivative, 4,5-dipiperidino-3-hydroxypyridazine.

Potentially, the pyridazine derivative of the invention may be a tautomer under equilibrium under certain conditions. In accordance with the invention, either one of them is described. A tautomer or a mixture with the tautomer may be satisfactory.

The pyridazine derivative of the invention includes 4,5-dipiperazinyl-3-hydroxypyridazine, 4,5-dipiperidino-3-hydroxypyridazine, 4,5-dihexahydroazepinyl-3-hydroxypyridazine, 4,5-dipyrrolidinyl-3-hydroxypyridazine, 4,5-bis(4-methylpiperazinyl)-3-hydroxypyridazine, 4,5-bis(bis(2-hydroxyethyl)amino)-3-hydroxypyridazine, 4,5-bis(tris(hydroxymethyl) methylamino)-3-hydroxypyridazin, 3-hydroxy-4-pyrrolidinylpyridazine, 3-hydroxy-5-pyrrolidinylpyridazine, 3-hydroxy-4-piperidinopyridazine, 3-hydroxy-5-piperidinopyridazine, 3-hydroxy-4-morpholinopyridazine, 3-hydroxy-5-morpholinopyridazine, 4-bis (2-hydroxyethyl)amino-3-hydroxypyridazine, 5-bis(2-hydroxyethyl)amino-3-hydroxypyridazine, 3-hydroxy-4-tris (hydroxymethyl)methylaminopyridazine, 3-hydroxy-5-tris (hydroxymethyl)methylaminopyridazine, 3-hydroxy-6-morpholinopyridazine, 3,6-bis(2-hydroxyethyl)pyridazine, 3,6-dimorpholinopyridazine, 4,5-dipyrrolidinyl-3-hydroxypyridazine hydrochloride salt, 4,5-dipiperidino-3-hydroxypyridazine hydrochloride salt, 3-hydroxy-5-piperidinopyridazine hydrochloride salt, 3-hydroxy-5-morpholinopyridazine hydrochloride salt, 5-bis(2-hydroxyethyl)amino-3-hydroxypyridazine hydrochloride salt, 3-hydroxy-5-tris(hydroxymethyl) methylaminopyridazine hydrochloride salt, 3-hydroxy-6-morpholinopyridazine hydrochloride salt, 3,6-bis(2-hydroxyethylamino)pyridazine hydrochloride salt, 4,5-bis (bis(2-hydroxyethyl)amino)-3-hydroxypyridazine hydrochloride salt, and 4,5-bis(tris(hydroxymethyl) methylamino)-3-hydroxypyridazine hydrochloride salt.

The pyridazine derivative of the invention is readily commercially available from ALDRICH CO., SIGMA CO., Tokyo Chemicals K.K. Otherwise, the pyridazine derivative can be synthetically prepared by known methods. Typical examples of the method for producing the derivative are shown below.

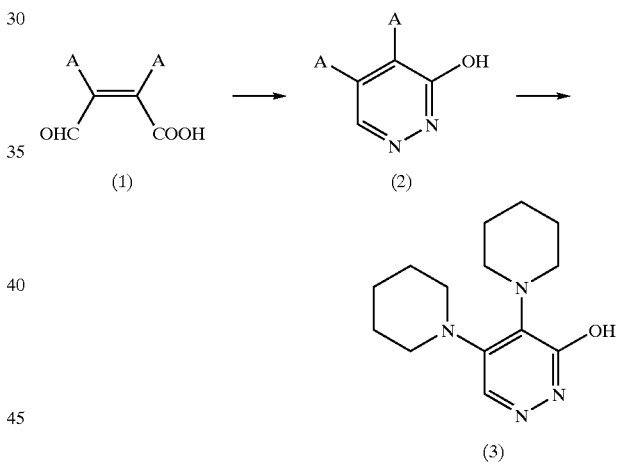

In the reaction formula, A represents chlorine atom or bromine atom.

According to the method described in Chemische Berichte, 32, 534 (1899) and the following reaction scheme, the compound (2) (4,5-dichloro-3-hydroxypyridazine provided that A is chlorine atom or 4,5-dibromo-3-hydroxypyridazine provided that A is bromine atom) can be prepared readily from the compound (1) readily available (mucochloric acid provided that A is chlorine atom or mucobromic acid provided that A is bromine atom). More specifically, the compound (2) can be readily prepared by subjecting the compound (1) (A is chlorine atom or bromine atom) to a ring-closure reaction with hydrazine. Further, the compound (2) is readily commercially available from ALDRICH CO. The pyridazine derivative of the invention can be produced by allowing the compound (2) (A is chlorine atom or bromine atom) to react with amines such as piperidine.

Herein, the pyridazine derivative of the invention can be prepared into an inorganic acid salt or an organic acid salt by known methods. The inorganic acid includes for example hydrochloric acid, sulfuric acid, phosphoric acid and hydrobromic acid. The organic acid includes for example acetic acid, lactic acid, maleic acid, fumaric acid, tartaric acid, citric acid, methanesulfonic acid, and p-toluenesulfonic acid.

Ultraviolet Absorbent and External Preparation for Skin

An ultraviolet absorbent containing the pyridazine derivative of the invention or a salt thereof as the main ingredient can be used in various products, preferably external preparations for skin. External preparations for skin in which the inventive ultraviolet absorbent is included can exert a great preventive effect against ultraviolet ray. Additionally, the ultraviolet absorbent is never decomposed under daylight exposure. Thus, the effect can be exerted in a stable manner for a long time. Furthermore, the ultraviolet absorbent never causes any skin trouble. Thus, the ultraviolet absorbent is useful for an external sunscreen preparation for skin.

So as to enhance the ultraviolet shielding effect of the external sunscreen preparation for skin, preferably, a combination of organic compound-based ultraviolet absorbents and inorganic compound-based ultraviolet shielding agents is used. Additionally, inorganic powders are frequently used in makeup cosmetics. However, an organic ultraviolet absorbent used in combination with inorganic powders may sometimes cause color change.

The ultraviolet absorbent of the invention can be used in combination with inorganic powders, because no color change occurs even if the ultraviolet absorbent is used together with inorganic powders in the external preparation for skin.

Inorganic Powders

Any inorganic powder may be satisfactory with no specific limitation, as long as the inorganic powder is generally used in cosmetics and medical supplies. For example, the inorganic powder includes inorganic powders such as talc, kaolin, boron nitride, mica, silk mica (sericite), white mica, black mica, gold mica, synthetic mica, vermiculite, magnesium carbonate, calcium carbonate, silicic anhydride, aluminium silicate, aluminium oxide, barium silicate, calcium silicate, magnesium silicate, metal tungstate salt, magnesium, silica, zeolite, barium sulfate, sintered calcium sulfate, plaster of Paris, calcium phosphate, fluorine apatite, hydroxyapatite, ceramic powder, and metal soap (zinc myristate, calcium palmitate, aluminum stearate, etc.), as well as inorganic pigments such as titanium dioxide, zinc oxide, iron oxide, iron titanate, carbon, lower-valent oxides of titanium, mango violet, cobalt violet, chromium oxide, chromium hydroxide, cobalt titanate, ultramarine blue, Prussian blue, titanium oxide-coated mica, titanium oxide-coated bismuth oxychloride, titanium oxide-coated talc, colored titanium oxide-coated mica, bismuth oxychloride, and fish scale guanine.

Photostabilizer

The pyridazine derivative of the invention and a salt thereof are useful as photostabilizers and highly optically stabilize dyes, perfume and drugs to be used in medical supplies and cosmetics, in particular. Additionally, the pyridazine derivative of the invention and a salt thereof can produce a photostabilizing effect synergistically enhanced when used in combination with sequestering agents.

Sequestering Agents

The sequestering agents to be used together with the pyridazine derivative and a salt thereof in accordance with the invention includes for example ethylenediaminetetraacetate (EDTA) sodium salt, ethylenediaminehydroxyethyltriacetate sodium, phosphoric acid, citric acid, ascorbic acid, succinic acid, gluconic acid, sodium polyphosphate, sodium metaphosphate, hydroxyethane diphosphonate salt, and etidronate salt.

Use of External Preparation for Skin

The external preparation for skin in accordance with the invention includes the above-mentioned ultraviolet absorbent and the above-mentioned photostabilizer. The external preparation for skin in accordance with the invention can be in any form with no specific limitation, as long as the external preparation can exert the effect of the invention. For example, the external preparation for skin can be in forms of skin care cosmetics such as skin lotion, emulsion, cream, and beauty lotion; makeup cosmetics such as base cosmetics, foundation, lipstick, face color, and eye liner; hair and scalp cosmetics such as hair spray, hair tonic and hair liquid; aromatic cosmetics such as perfume and eau de cologne; and shampoo and rinse.

The Quantities of the Pyridazine Derivative and a Salt Thereof to be Blended in the External Preparation for Skin For blending the pyridazine derivative and a salt thereof in accordance with the invention in the external preparation for skin, the quantities thereof can appropriately be determined, depending on the intended ultraviolet absorption or photostabilization potency. The pyridazine derivative and a salt thereof are blended at preferably 0.001 to 20 wt %, more preferably 0.01 to 10 wt % in a composition. Below 0.001 wt %, the ultraviolet preventive effect or the photostabilization effect sometimes cannot be sufficiently obtained. Above 20 wt %, unpreferably, the resulting dosage form can be retained with much difficulty.

Other Ingredients

In the external preparation for skin in accordance with the invention can include other ingredients, if necessary, which can generally be included in cosmetics and medical supplies. For example, the ingredients are liquid fats and oils, solid fats and oils, wax, hydrocarbon, higher fatty acid, higher alcohol, esters, silicone, anionic surfactants, cationic surfactants, amphoteric surfactants, nonionic surfactants, moisturizer, water-soluble polymer compound, thickener, coating agent, lower alcohol, polyvalent alcohol, sugars, amino acids, organic amines, pH adjuster, skin nutritious supplements, vitamins, antioxidant, perfume, powder, coloring agent, and water, in addition to the essential ingredients. Furthermore, an ultraviolet absorbent and a photostabilizer other than the pyridazine derivative of the invention may be combined unless the ultraviolet absorbent and the photostabilizer disadvantageously affect the effect of the invention.

Ultraviolet-Absorbing Composition

Additionally, the ultraviolet absorbent of the invention can be blended in products including for example paints, dyes, pigments, various resins, synthetic rubber, latex, film, fiber and glass other than the external preparation for skin, to prepare the products into photostabilized compositions. Because the pyridazine derivative of the invention has such a great thermostability that the pyridazine derivative never vaporizes, the effect can be retained for a long time. In this case, generally, the pyridazine derivative can be blended at a quantity of preferably 0.001 to 20 wt %, more preferably 0.01 to 10 wt %. Below 0.001 wt %, the resulting photostabilizing effect sometimes may be insufficient. Above 20 wt %, the resulting products are molded with much difficulty, unpreferably.

The invention is described in more detail in the following specific examples. Herein, the invention is not limited to these examples.

First, the pyridazine derivative of the invention is shown in the following Production Examples.

PRODUCTION EXAMPLE 1
4,5-Dipiperidino-3-hydroxypyridazine 4,5-Dichloro-3-hydroxypyridazine (25.0 g; 0.151 mol) was dissolved in piperidine (120 mol), under reflux condition for 24 hours. After cooling, the deposited crystal was filtered, to give 4,5-dipiperidino-3-hydroxypyridazine in white crystal (30.3 g as a yield of 75%).

$^1$H-NMR (DMSO-$d_6$, TMS, ppm) δ: 1.56–1.78 (m, 12H: piperidine ring: —N—CH$_2$—CH$_2$—CH$_2$—CH$_2$—CH$_2$—N—x2) 3.16 (t, 4H, J=5.2 Hz, piperidine ring: —CH$_2$—N—CH$_2$—) 3.26 (t, 4H, J=5.2 Hz, piperidine ring: —CH$_2$—N—CH$_2$—) 7.57 (s, 1H, pyridazine ring, H-6), 10.32 (s, 1H, OH)

MS spectrum: MW=262 ($C_{14}H_{22}N_4O$=262.36)

PRODUCTION EXAMPLE 2
6-Morpholino-3-hydroxypyridazine

6-Chloro-3-hydroxypyridazine (25.0 g, 0.191 mol) was dissolved in morpholine (120 mol), under reflux condition for 24 hours. After cooling, the deposited crystal was filtered, to give 6-morpholino-3-hydroxypyridazine in white crystal (25.8 g as a yield of 74%).

$^1$H-NMR (DMSO-$d_6$, TMS, ppm) δ: 3.15 (t, 4H, J=4.8 Hz, —CH$_2$—N—CH$_2$—) 3.67 (t, 4H, J=4.8 Hz, —CH$_2$—O—CH$_2$—) 6.79 (d, 1H, J=10.4 Hz, pyridazine ring, H-4 or H-5) 7.49 (d, 1H, J=10.4 Hz, pyridazine ring, H-4 or H-5) 12.13 (s, 1H, OH)

MS spectrum: MW=181 ($C_8H_{11}N_3O_2$=181.19)

PRODUCTION EXAMPLE 3
3,6-Dimorpholinopyridazine 3,6-Dichloropyridazine (25.0 g, 0.168 mol) was dissolved in morpholine (120 mol), for reflux condition for 24 hours. After cooling, the deposited crystal was filtered, to give 3,6-dimorpholinopyridazine in white crystal (33.7 g as a yield of 80%).

$^1$H-NMR (DMSO-$d_6$, TMS, ppm) δ: 3.42 (t, 8H, J=4.8 Hz, —CH$_2$—N—CH$_2$—) 3.80 (t, 8H, J=4.8 Hz, —CH$_2$—O—CH$_2$—) 6.92 (s, 2H, pyridazine ring H-4 or H-5)

MS spectrum: MW=250 ($C_{12}H_{18}N_4O_2$=250.30)

The test of the ultraviolet absorption of the pyridazine derivative of the invention is now described.

TEST EXAMPLE 1
Absorbance

Figure 2:
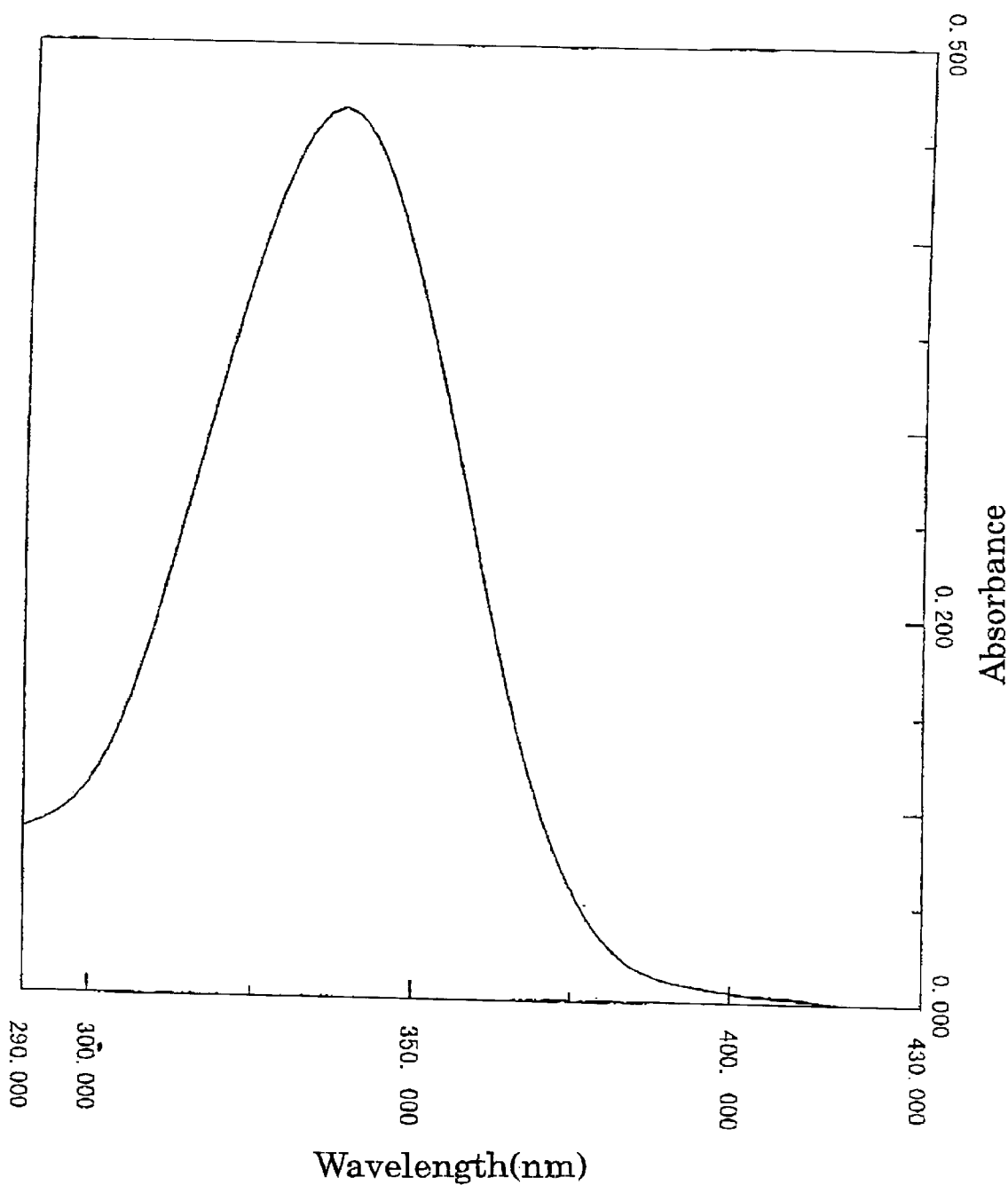
FIG. 2 is an ultraviolet absorption spectrum of the inventive pyridazine derivative, 3-hydroxy-4-piperidinopyridazine.
Figure 3:
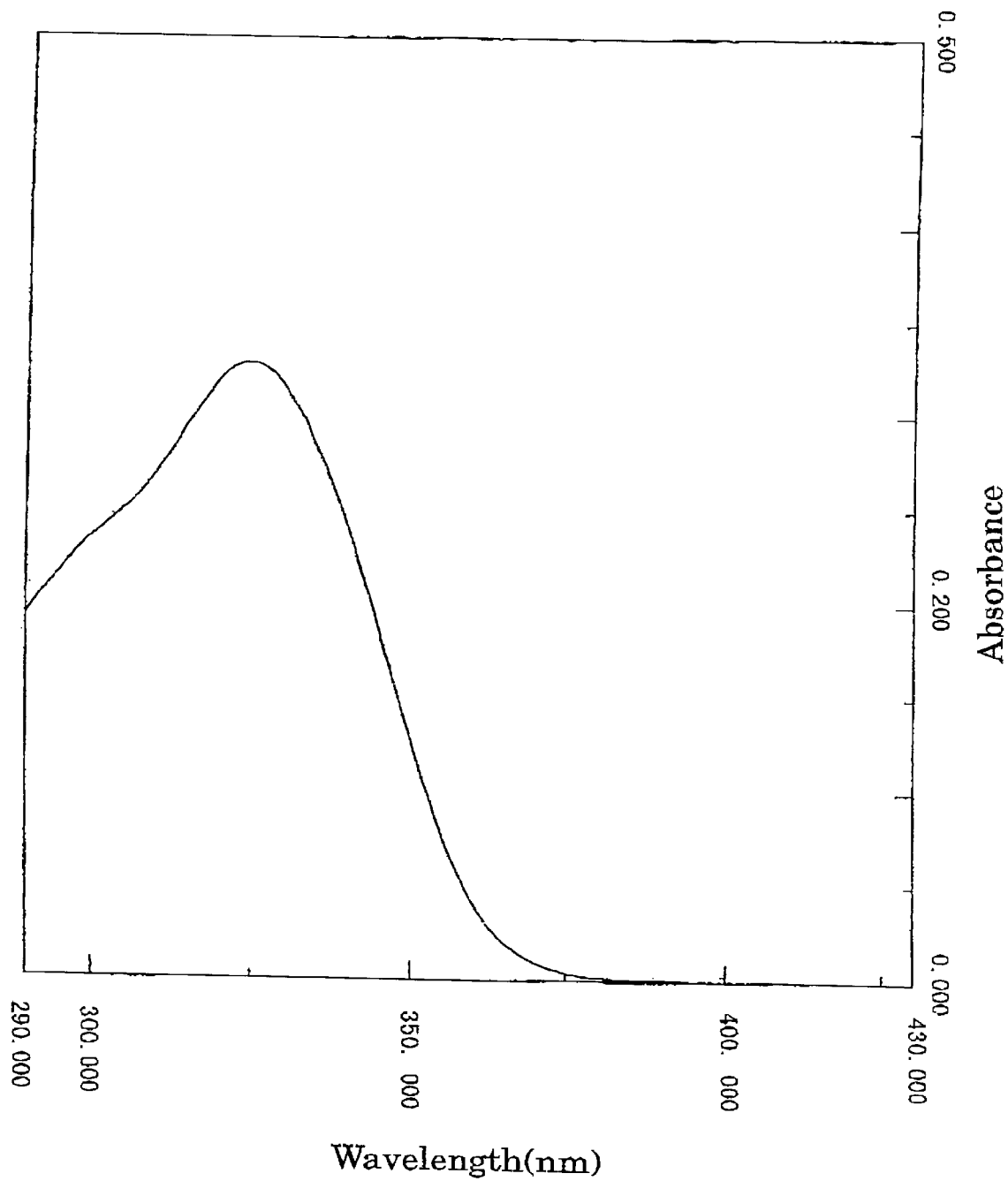
FIG. 3 is an ultraviolet absorption spectrum of the inventive pyridazine derivative, 3-hydroxy-5-piperidinopyridazine.
Figure 4:
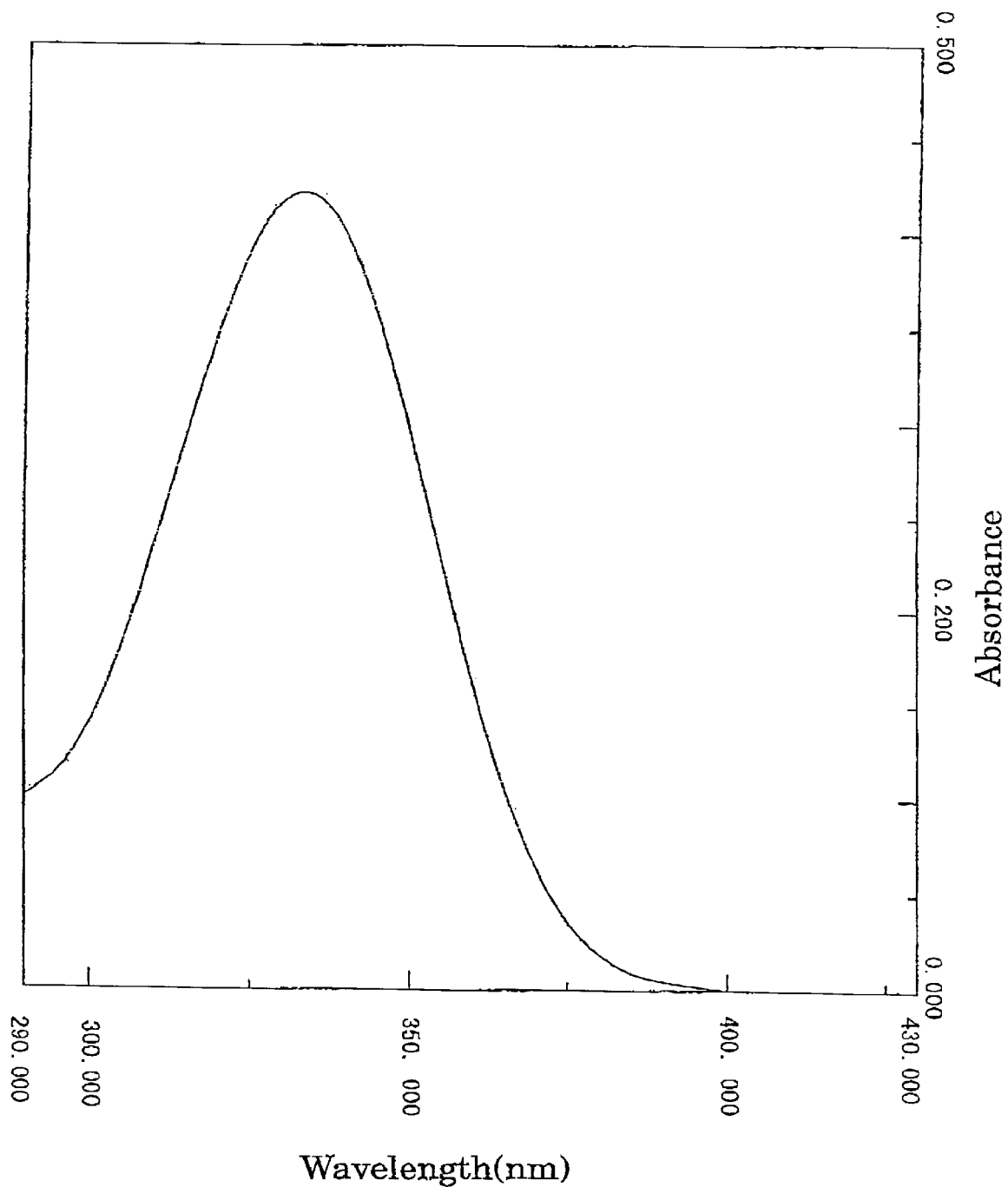
FIG. 4 is an ultraviolet absorption spectrum of the inventive pyridazine derivative, 3-hydroxy-4-morpholinopyridazine.
Figure 5:
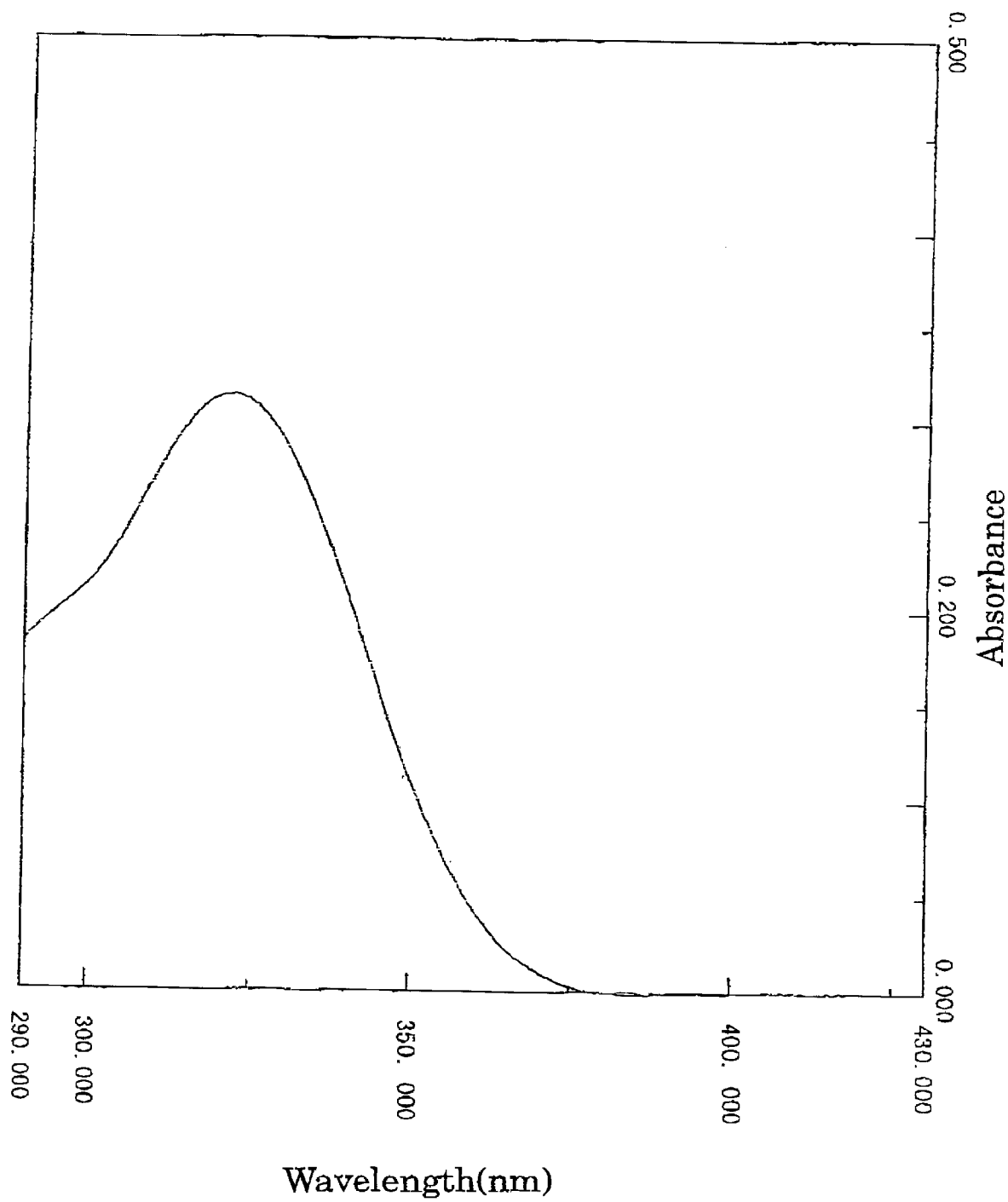
FIG. 5 is an ultraviolet absorption spectrum of the inventive pyridazine derivative 3-hydroxy-5-morpholinopyridazine.
Figure 6:
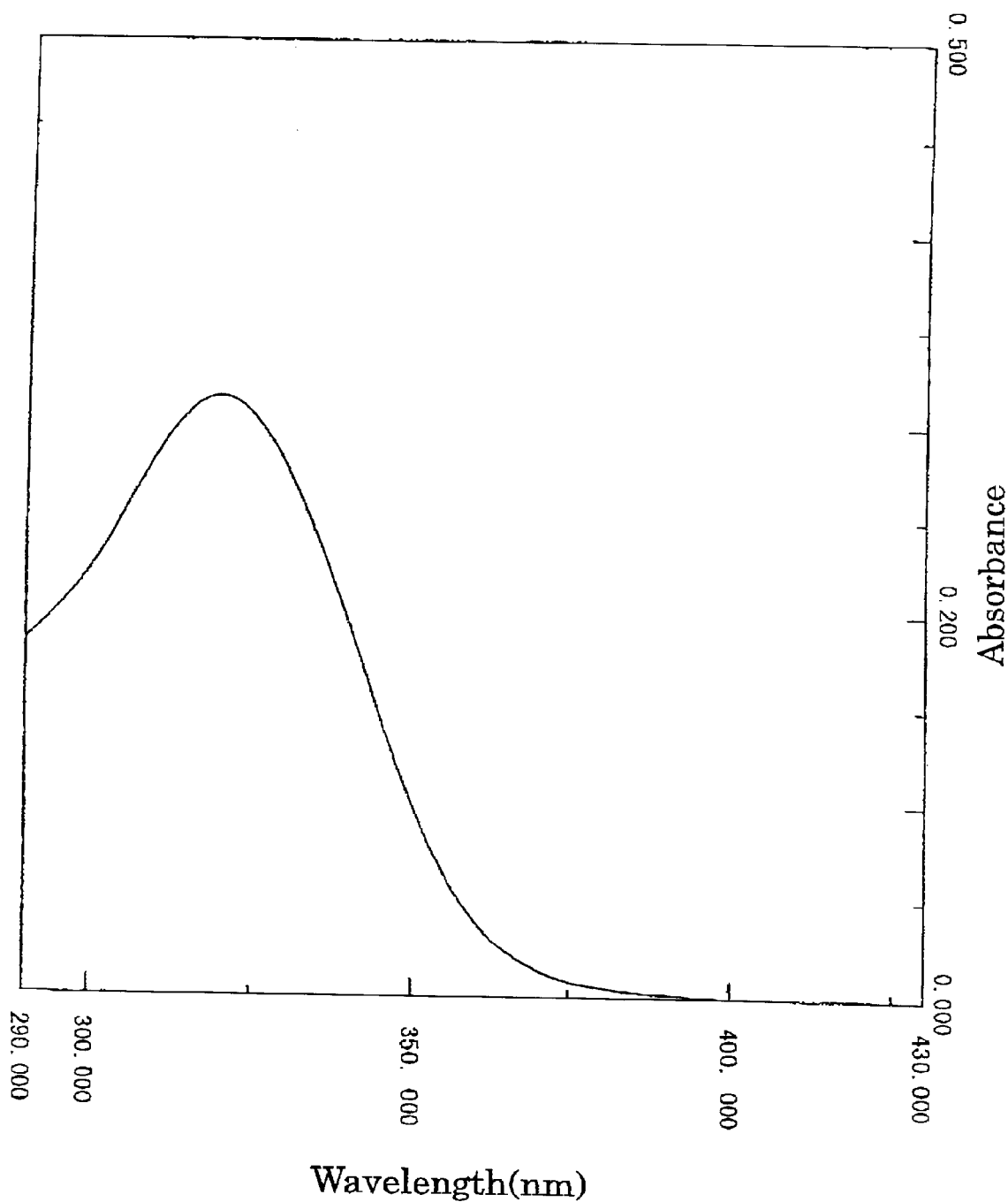
FIG. 6 is an ultraviolet absorption spectrum of the inventive pyridazine derivative, 5-bis(2-hydroxyethyl)amino-3-hydroxypyridazine.
Figure 7:
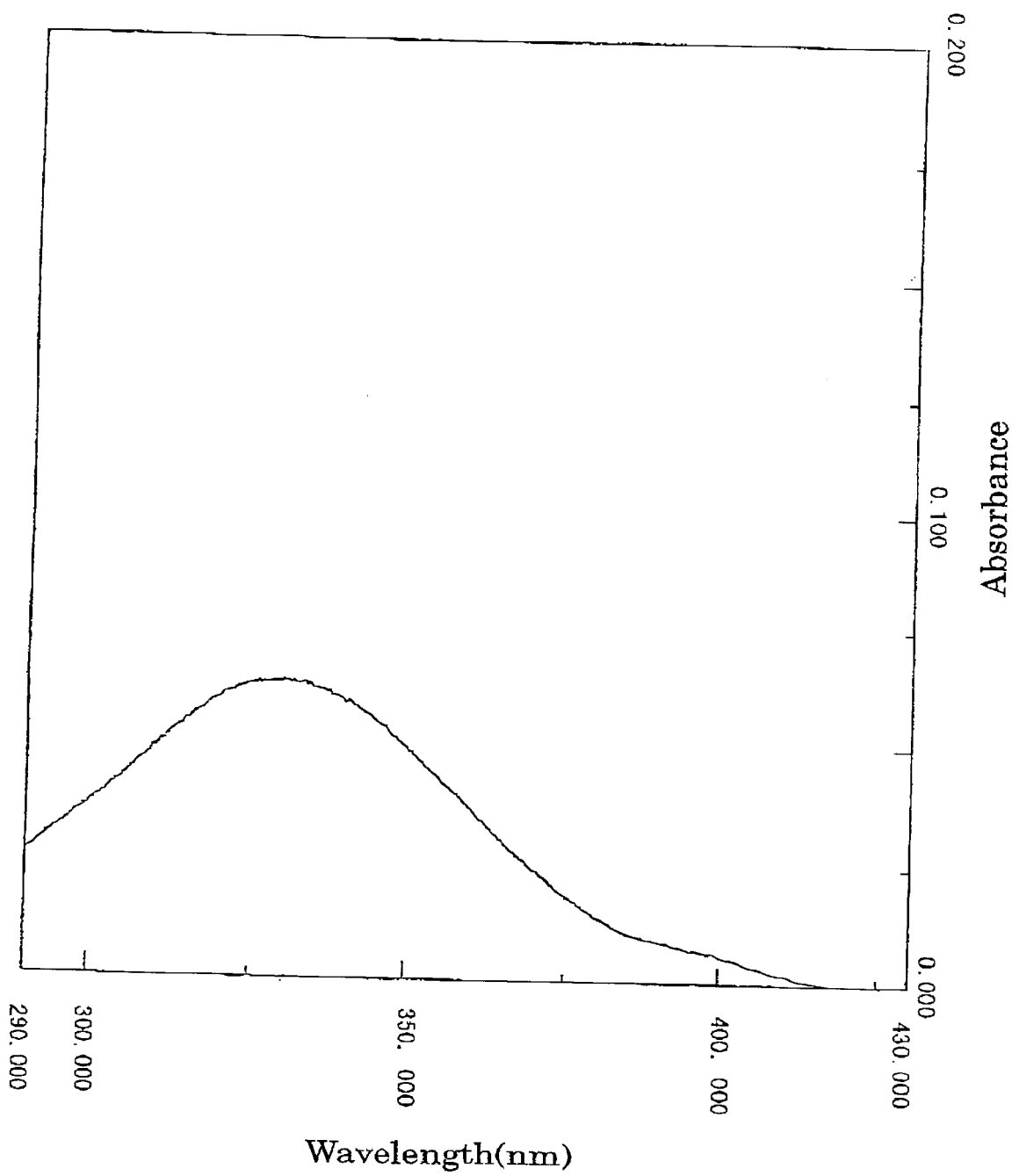
FIG. 7 is an ultraviolet absorption spectrum of the inventive pyridazine derivative, 3-hydroxy-6-morpholinopyridazine.
Figure 8:
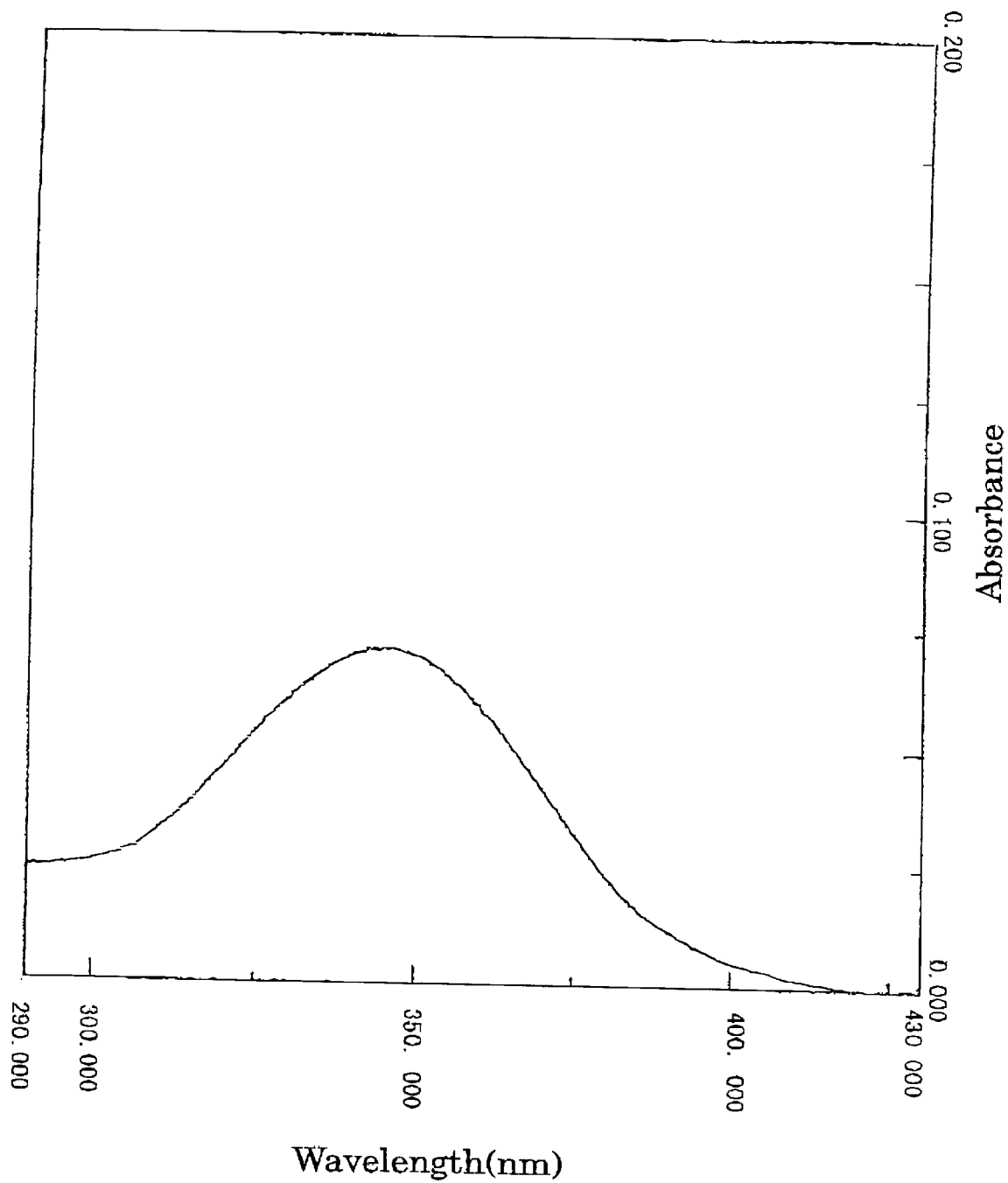
FIG. 8 is an ultraviolet absorption spectrum of the inventive pyridazine derivative, 3,6-bis(2-hydroxyethylamino) pyridazine.
Figure 9:
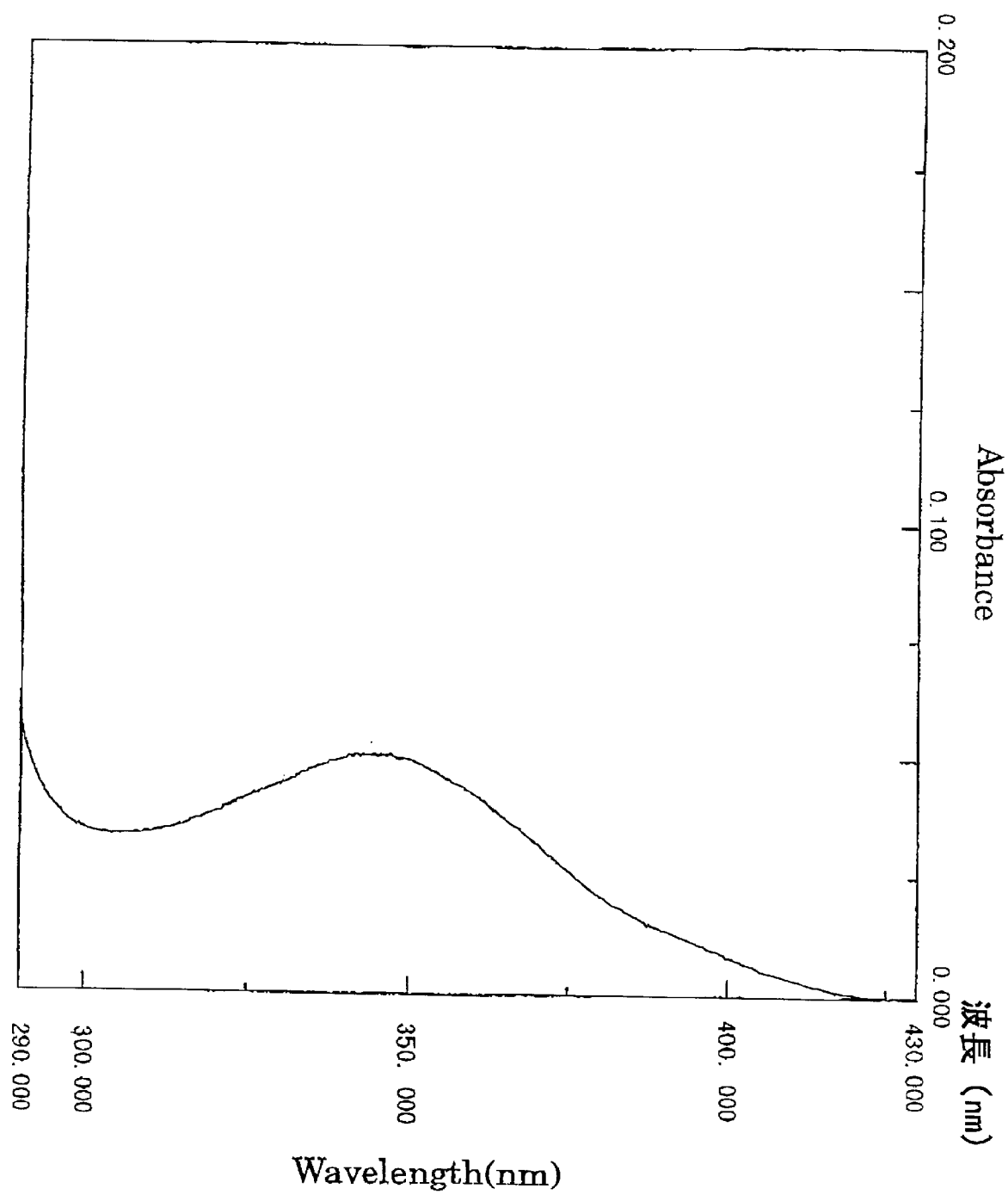
FIG. 9 is an ultraviolet absorption spectrum of the inventive pyridazine derivative, 3,6-dimorpholinopyridazine.

The ultraviolet absorption spectra (solvent: water; 10 ppm concentration; optical path length of 1 cm) of 4,5-dipiperidino-3-hydroxypyridazine, 3-hydroxy-4-piperidinopyridazine, 3-hydroxy-5-piperidinopyridazine, 3-hydroxy-4-morpholinopyridazine, 3-hydroxy-5-morpholinopyridazine, 5-bis(2-hydroxyethyl)amino-3-hydroxypyridazine, 3-hydroxy-6-morpholinopyridazine, 3,6-bis(2-hydroxyethylamino)pyridazine, and 3,6-dimorpholinopyridazine were measured with a spectrophotometer (Ube st-55 manufactured by JASCO CO., LTD.) The results are shown in FIGS. 1 to 9.

As shown in FIGS. 1 to 9, the pyridazine derivative of the invention can sufficiently absorb 290–400 nm ultraviolet ray reaching the ground surface nearly over the whole range of the wavelengths and hardly absorbs a visible wavelength range above 400 nm. Thus, the pyridazine derivative of the invention can attain excellent transparency.

TEST EXAMPLE 2
Ultraviolet Preventive Effect (i) Test Method

An application test was carried out on beach in summer. Equal volumes of samples were individually coated on back halves of subjects. After exposure to direct daylight, the degree of sunburn was assessed according to the following assessment standards. Each group consists of 10 subjects.

Assessment Standards

Prominently effective: none or almost no sunburn symptom was observed.

Effective: light sunburn symptom was observed.

Ineffective: strong sunburn symptom was observed.

Assessment

◎: prominently effective or effective for 80% or more of the subjects.

○: prominently effective or effective for 50% or more to less than 80% of the subjects.

Δ: prominently effective or effective for 30% or more to less than 50% of the subjects.

x: prominently effective or effective for less than 30% of the subjects.

(ii) Sample Preparation a. Lotion

| Alcohol phase | |
|---|---|
| 95% Ethanol: | 25.0 wt % |
| POE (25) - Hydrogenated castor oil: | 2.0 |
| Ultraviolet absorbent (described in Table 1) | 0 to 20 |
| Preservative | appropriate volume |
| Fragrance | appropriate volume |
| Aqueous phase | |
| Glycerin | 5.0 |
| Sodium hexametaphosphate | appropriate volume |
| Ion exchanger water | qs |

Production Process

The aqueous phase and the alcohol phase were separately prepared and then mixed together.

b. Cream

| | |
|---|---|
| Stearyl alcohol | 7.0 wt % |
| Stearic acid | 2.0 |
| Hydrogenated lanolin | 2.0 |
| Squalene | 5.0 |
| 2-Octyldodecyl alcohol | 6.0 |
| POE (25) cetyl alcohol | 3.0 |
| Glycerin monostearate ester | 2.0 |
| Propylene glycol | 5.0 |
| Ultraviolet absorbent (described in Table 2) | 0 to 20 |
| Perfume | appropriate volume |
| Sodium hydrogen sulfite | 0.03 |
| Ethylparaben | 0.3 |
| Ion exchange water | qs |

Production Process

Propylene glycol was added to and dissolved in ion exchange water. The resulting solution was retained at 70° C. under heating (aqueous phase). Other ingredients were mixed with the solution. The resulting mixture was melted under heating and retained at 70° C. (oil phase). The oil phase was added to the aqueous phase, for preliminary emulsification with a homomixer to homogeneity. Under thorough mixing, subsequently, the mixture was cooled to 30° C.

(iii) Results

The results of the lotion described in a. and the cream described in b. are shown in Table 2.

TABLE 1 a. Lotion

| Ultraviolet absorbent | Blend amount (wt %) | Ultraviolet prevention effect |
|---|---|---|
| 4,5-Dipiperidino-3-hydroxypyridazine | 20 | ⊚ |
|  | 10 | ⊚ |
|  | 5 | ⊚ |
|  | 1 | ⊚ |
|  | 0.01 | ⊚ |
|  | 0.001 | ○ |
|  | 0.0005 | Δ |
| 3-Hydroxy-5-morpholinopyridazine | 20 | ⊚ |
|  | 10 | ⊚ |
|  | 5 | ⊚ |
|  | 1 | ⊚ |
|  | 0.01 | ⊚ |
|  | 0.001 | ○ |
|  | 0.0005 | Δ |
| 3-Hydroxy-4-piperidinopyridazine | 20 | ⊚ |
|  | 10 | ⊚ |
|  | 5 | ⊚ |
|  | 1 | ⊚ |
|  | 0.01 | ⊚ |
|  | 0.001 | ○ |
|  | 0.0005 | Δ |
| no included | — | X |

TABLE 2 b. cream

| Ultraviolet absorbent | Blend amount (wt %) | Ultraviolet prevention effect |
|---|---|---|
| 4,5-Dipiperidino-3-hydroxypyridazine | 20 | ⊚ |
|  | 10 | ⊚ |
|  | 5 | ⊚ |
|  | 1 | ⊚ |
|  | 0.01 | ⊚ |
|  | 0.001 | ○ |
|  | 0.0005 | Δ |
| 3-Hydroxy-5-morpholinopyridazine | 20 | ⊚ |
|  | 10 | ⊚ |
|  | 5 | ⊚ |
|  | 1 | ⊚ |
|  | 0.01 | ⊚ |
|  | 0.001 | ○ |
|  | 0.0005 | Δ |
| 3-Hydroxy-4-piperidinopyridazine | 20 | ⊚ |
|  | 10 | ⊚ |
|  | 5 | ⊚ |
|  | 1 | ⊚ |
|  | 0.01 | ⊚ |
|  | 0.001 | ○ |
|  | 0.0005 | Δ |
| No included | — | X |

As apparently shown in tables 1 and 2, the external preparations for skin where the pyridazine derivative of the invention was blended had excellent ultraviolet prevention effect. Additionally, the tables show that the amount of the pyridazine derivative of the invention and/or a salt thereof in blend is preferably 0.001 to 20 wt %. Further, it is very pharmaceutically difficult to prepare any formulation at a blend amount of 20 wt % or more.

As described above, the pyridazine derivative of the invention has excellent absorption over a wide ultraviolet range. So as to examine whether or not the pyridazine derivative of the invention can be blended as an ultraviolet absorbent in an external preparation for skin, furthermore, skin irritation, photostability and the influence of inorganic powders were additionally examined.

TEST EXAMPLE 3

Test of Skin Irritation

The same samples as in the Test Example 2 were used (at a 10 wt % amount of an ultraviolet absorbent).

(i) Continuous Application Test

Continuous application test was carried out for 20 healthy subjects per one group. An appropriate amount of each of the samples was coated twice daily for 4 weeks. The effects were assessed according to the following assessment standards.

Assessment Standards

| Degree of skin reaction | Score |
|---|---|
| No symptom (negative) | 0 |
| Light (false-negative) | 1 |
| Mild (weakly positive) | 2 |
| Moderate (moderately positive) | 3 |
| Severe (highly positive) | 4 |

Assessment

Mean score was calculated for the determination of the effect on the basis of the following standards.

⊚: mean score of 0.

○: mean score of more than 0 to less than 1.

Δ: mean score of 1 or more to less than 2.

x: mean score of 2 or more.

Results

The results are shown in the following table.

TABLE 3

| Ultraviolet absorbent | Dosage form | Determination |
|---|---|---|
| 4,5-Dipiperidino-3-hydroxypyridazine | lotion | ⊚ |
|  | cream | ⊚ |
| 3-Hydroxy-5-morpholinopyridazine | lotion | ⊚ |
|  | cream | ⊚ |
| 3-Hydroxy-4-piperidinopyridazine | lotion | ⊚ |
|  | cream | ⊚ |
| No included | lotion | ⊚ |
|  | cream | ⊚ |

(ii) Patch Test

20 Healthy male and female volunteers per one group were carried out in a 24-hour occlusion patch test, using a fin chamber on forearm curves. Assessment was done on the basis of the following assessment standards.

Assessment Standards

| Degree of skin reaction | Score |
|---|---|
| No reaction (negative) | 0 |
| Light erythema (false-negative) | 1 |
| Erythema (weakly positive) | 2 |
| Erythema + edema (moderately positive) | 3 |
| Erythema + edema + papule (highly positive) | 4 |
| Large blister (most highly positive) | 5 |

Assessment

Mean score was determined for the assessment on the basis of the following standards.

⊚: mean score of 0.
○: mean score of more than 0 to less than 1.
Δ: mean score of 1 or more to less than 2.
x: mean score of 2 or more.

Results

The results are shown in the following table.

TABLE 4

| Ultraviolet absorbent | Dosage form | Determination |
|---|---|---|
| 4,5-Dipiperidino-3-hydroxypyridazine | lotion | ⊚ |
| | cream | ⊚ |
| 3-Hydroxy-5-morpholinopyridazine | lotion | ⊚ |
| | cream | ⊚ |
| 3-Hydroxy-4-piperidinopyridazine | lotion | ⊚ |
| | cream | ⊚ |
| No included | lotion | ⊚ |
| | cream | ⊚ |

As apparently shown in Tables 3 and 4, the external preparations for skin where the ultraviolet absorbents of the invention were blended did not irritate skin at the continuous application test and the patch test, indicating that the external preparations for skin had very excellent safety.

TEST EXAMPLE 4

Photostability Test

Aqueous solutions of the pyridazine derivative of the invention were exposed to daylight for 2 weeks (at a daylight exposure of 80 MJ). Subsequently, the remaining ratio and the change of the appearance were examined to measure the ultraviolet spectra with a spectrophotometer (solvent: water; concentration of 10 ppm and optical path length of 1 cm). The area under ultraviolet spectra curve from 290 nm to 400 nm were determined by integration to compare the area with the area before daylight exposure.

Determination

The remaining ratio and the change of the area under the ultraviolet spectrum were determined on the basis of the following standards.

⊚: 95% or more of those before daylight exposure.
○: 90% or more to less than 95% of those before daylight exposure.
Δ: 70% or more to less than 90% of those before daylight exposure.
x: less than 70% of those before daylight exposure.

TABLE 5

| Ultraviolet absorbent | Remaining ratio | Change of area under ultraviolet spectrum |
|---|---|---|
| 4,5-Dipiperidino-3-hydroxypyridazine | ⊚ | ⊚ |
| 3-Hydroxy-5-morpholinopyridazine | ⊚ | ⊚ |
| 3-Hydroxy-4-piperidinopyridazine | ⊚ | ⊚ |

As indicated in Table 5, the pyridazine derivative of the invention was never decomposed even under direct daylight exposure for a long time but was at very high remaining ratios. Furthermore, no change was observed in the shapes or areas of the ultraviolet spectra. Even apparently, no coloring or deposition was observed.

TEST EXAMPLE 5

The Stability Test in Combination with Inorganic Powder-Based Ultraviolet Shielding Agent A sunscreen cream of the following formulation was prepared and stored at 50° C. for 2 months. Under visual observation of the color change, the stability of the inventive pyridazine derivative in combination with inorganic powder-based ultraviolet screening agents commonly in blend as external preparations for skin for the purpose of ultraviolet prevention was examined.

| Formulation Sunscreen cream | |
|---|---|
| 1. Ethyl cellulose | 1.0 wt % |
| 2. Ethanol | 5.0 |
| 3. 2-Ethylhexylsuccinate | 24.0 |
| 4. Titanium dioxide | 1.0 |
| 5. Porous silicic anhydride powder | 1.0 |
| 6. Spherical nylon powder | 1.0 |
| 7. Talc | 1.0 |
| 8. Sericite | 1.0 |
| 9. Boron nitride | 1.0 |
| 10. Silicone-treated mica | 1.0 |
| 11. Ultraviolet absorbent (described in Table 6) | 10.0 |
| 12. Carboxymethyl cellulose | 1.0 |
| 13. Ion exchange water | qs |
| 14. Preservative | appropriate amount |
| 15. Perfume | appropriate amount |

Production Process

After the ingredient 2 was added to the ingredient 1 to swell the ingredient 2, the ingredients 3 to 11 were mixed with the resulting mixture under heating, for sufficient dispersion and dissolution. While keeping the dispersion at 70° C., a solution of the mixture of the ingredients 12 to 15 was gradually added to the dispersion under thorough emulsification with a homomixer. The resulting mixture was cooled to 30° C. under sufficient stirring to prepare sunscreen creams.

Results

The results are shown in the following table.

TABLE 6

| Ultraviolet absorbent | Color change |
|---|---|
| 4,5-Dipiperidino-3-hydroxypyridazine | no |
| 3-Hydroxy-5-morpholinopyridazine | no |
| 3-Hydroxy-4-piperidinopyridazine | no |

As apparently shown in Table 6, no color change of the pyridazine derivative of the invention even in combination with these inorganic powders was observed.

As described above, the pyridazine derivative of the invention has no skin irritation and great photostability, with no color change when used in combination with inorganic powders. Thus, the pyridazine derivative of the invention is very useful as ultraviolet absorbents which can be blended in external preparations for skin.

The effect of the pyridazine derivative of the invention as a photostabilizer was then examined.

First, the photostabilization effect on each dye and the change of the appearance of each composition were examined, by using the following formulation for assessment.

TEST EXAMPLES 6–91

Formulations for Assessment of Dye Stabilization Effect

| Name of raw material | Blend amount (wt %) |
|---|---|
| Ion exchange water | to 100 |
| Brucine-modified alcohol | 5 |
| Glycerin | 5 |
| Dipropylene glycol | 5 |
| Polyoxyethylene-hydrogenated castor oil | 1 |
| Methylparaben | 0.2 |
| Lactic acid | 0.006 |
| Sodium lactate | 0.2 |
| Photostabilizer (described in Tables 7 to 9) | described in tables 7 to 9 |
| Dye (described in Tables 7 to 9) | described in tables 7 to 9 |
| Total | 100 |

For observation of the change of the appearance of each test sample (determination based on visual observation) and the measurement of color difference (ΔE) before and after daylight exposure (80 MJ), the test sample was prepared.

With a spectrophotometer, the color was measured on the Lab coordinate system, to calculate the color difference on the basis of the color before daylight exposure. More specifically, the color difference (ΔE) was calculated on the basis of the measured values ($L_1$, $a_1$, $b_1$) before daylight exposure.

$$\Delta E = [(L_2-L_1)^2 + (a_2-a_1)^2 + (b_2-b_1)^2]^{1/2}$$

The results are shown in Tables 7 to 9.

TABLE 7

| Test Example | Dye Compounds | blend amount | Photostabilizer Compounds | blend amount | Daylight exposure (80 MJ) ΔE | Appearance (visual determination) |
|---|---|---|---|---|---|---|
| 6 | Red 227 | 0.0001 | none | 0 | 1.45 | x |
| 7 | (Acid Fuchsine D) | | 4,5-Dipiperidino-3-hydroxypyridazine | 0.05 | 0.53 | ○ |
| 8 | | | 3-Hydroxy-4-piperidinopyridazine | 0.05 | 0.54 | ○ |
| 9 | | | 3-Hydroxy-5-piperidinopyridazine | 0.05 | 0.52 | ○ |
| 10 | | | 3-Hydroxy-4-morpholinopyridazine | 0.05 | 0.60 | ○ |
| 11 | | | 3-Hydroxy-5-morpholinopyridazine | 0.05 | 0.52 | ○ |
| 12 | | | 3-Hydroxy-6-morpholinopyridazine | 0.05 | 0.54 | ○ |
| 13 | | | 3,6-Dimorpholinopyridazine | 0.05 | 0.53 | ○ |
| 14 | | | 3,6-Bis(2-hydroxyethylamino)pyridazine | 0.05 | 0.64 | ○ |
| 15 | | | 5-Bis(2-hydroxyethyl)amino-3-hydroxypyridazine | 0.05 | 0.55 | ○ |
| 16 | | | 2-Hydroxy-4-methoxybenzophenone | 0.05 | 0.71 | Δ |
| 17 | | | 2-Hydroxy-4-methoxybenzophenone-5-sulfonate sodium | 0.05 | 0.80 | Δ |
| 18 | | | p-Methoxycinnamate octyl | 0.05 | 1.22 | x |
| 19 | | | 4-tert-Butyl-4'-methoxydibenzoylmethane | 0.05 | 0.95 | Δ |
| 20 | Yellow 5 | 0.001 | none | 0 | 1.83 | x |
| 21 | (Sunset Yellow FCF) | | 4,5-Dipiperidino-3-hydroxypyridazine | 0.05 | 0.55 | ○ |
| 22 | | | 3-Hydroxy-4-piperidinopyridazine | 0.05 | 0.58 | ○ |
| 23 | | | 3-Hydroxy-5-piperidinopyridazine | 0.05 | 0.53 | ○ |
| 24 | | | 3-Hydroxy-4-morpholinopyridazine | 0.05 | 0.62 | ○ |
| 25 | | | 3-Hydroxy-5-morpholinopyridazine | 0.05 | 0.52 | ○ |
| 26 | | | 3-Hydroxy-6-morpholinopyridazine | 0.05 | 0.53 | ○ |
| 27 | | | 3,6-Dimorpholinopyridazine | 0.05 | 0.51 | ○ |
| 28 | | | 3,6-Bis(2-hydroxyethylamino)pyridazine | 0.05 | 0.66 | ○ |
| 29 | | | 5-Bis(2-hydroxyethyl)amino-3-hydroxypyridazine | 0.05 | 0.65 | ○ |
| 30 | | | 2-Hydroxy-4-methoxybenzophenone | 0.05 | 0.82 | Δ |
| 31 | | | 2-Hydroxy-4-methoxybenzophenone-5-sulfonate sodium | 0.05 | 0.78 | Δ |
| 32 | | | p-Methoxycinnamate octyl | 0.05 | 1.56 | x |
| 33 | | | 4-tert-Butyl-4'-methoxydibenzoylmethane | 0.05 | 0.88 | Δ |

Determination of appearance
○: no change;
Δ: almost no change;
x: change

TABLE 8

| Test Example | Dye Compounds | Blend amount | Photostabilizer Compounds | Blend amount | Daylight exposure (80 MJ) ΔE | Appearance (visual determination) |
|---|---|---|---|---|---|---|
| 34 | Blue 1 | 0.0001 | none | 0 | 8.92 | x |
| 35 | (Brilliant Blue FCF) | | 4,5-Dipiperidino-3-hydroxypyridazine | 0.05 | 1.22 | ○ |
| 36 | | | 3-Hydroxy-4-piperidinopyridazine | 0.05 | 1.24 | ○ |
| 37 | | | 3-Hydroxy-5-piperidinopyridazine | 0.05 | 1.28 | ○ |

TABLE 8-continued

| | Dye | | Photostabilizer | | Daylight exposure (80 MJ) | |
|---|---|---|---|---|---|---|
| Test Example | Compounds | Blend amount | Compounds | Blend amount | Δ E | Appearance (visual determination) |
| 38 | | | 3-Hydroxy-4-morpholinopyridazine | 0.05 | 1.26 | ○ |
| 39 | | | 3-Hydroxy-5-morpholinopyridazine | 0.05 | 1.31 | ○ |
| 40 | | | 3-Hydroxy-6-morpholinopyridazine | 0.05 | 1.32 | ○ |
| 41 | | | 3,6-Dimorpholinopyridazine | 0.05 | 1.25 | ○ |
| 42 | | | 3,6-Bis(2-hydroxyethylamino)pyridazine | 0.05 | 1.38 | ○ |
| 43 | | | 5-Bis(2-hydroxyethyl)amino-3-hydroxypyridazine | 0.05 | 1.29 | ○ |
| 44 | | | 2-Hydroxy-4-methoxybenzophenone | 0.05 | 1.76 | Δ |
| 45 | | | 2-Hydroxy-4-methoxybenzophenone-5-sulfonate sodium | 0.05 | 1.67 | Δ |
| 46 | | | p-Methoxycinnamate octyl | 0.05 | 5.23 | x |
| 47 | | | 4-tert-Butyl-4'-methoxydibenzoylmethane | 0.05 | 1.49 | Δ |
| 48 | Green 3 | 0.001 | none | 0 | 2.12 | x |
| 49 | (Fast Green FCF) | | 4,5-Dipiperidino-3-hydroxypyridazine | 0.05 | 0.45 | ○ |
| 50 | | | 3-Hydroxy-4-piperidinopyridazine | 0.05 | 0.46 | ○ |
| 51 | | | 3-Hydroxy-5-piperidinopyridazine | 0.05 | 0.45 | ○ |
| 52 | | | 3-Hydroxy-4-morpholinopyridazine | 0.05 | 0.48 | ○ |
| 53 | | | 3-Hydroxy-5-morpholinopyridazine | 0.05 | 0.48 | ○ |
| 54 | | | 3-Hydroxy-6-morpholinopyridazine | 0.05 | 0.43 | ○ |
| 55 | | | 3,6-Dimorpholinopyridazine | 0.05 | 0.44 | ○ |
| 56 | | | 3,6-Bis(2-hydroxyethylamino)pyridazine | 0.05 | 0.63 | ○ |
| 57 | | | 5-Bis(2-hydroxyethyl)amino-3-hydroxypyridazine | 0.05 | 0.62 | ○ |
| 58 | | | 2-Hydroxy-4-methoxybenzophenone | 0.05 | 0.75 | Δ |
| 59 | | | 2-Hydroxy-4-methoxybenzophenone-5-sulfonate sodium | 0.05 | 0.74 | Δ |
| 60 | | | p-Methoxycinnamate octyl | 0.05 | 1.64 | x |
| 61 | | | 4-tert-Butyl-4'-methoxydibenzoylmethane | 0.05 | 0.62 | Δ |

Determination of appearance
○: no change;
Δ: almost no change;
x: change

TABLE 9

| | Dye | | Photostabilizer | | Daylight exposure (80 MJ) | |
|---|---|---|---|---|---|---|
| Test Example | Compounds | Blend amount | Compounds | Blend amount | Δ E | Appearance (visual determination) |
| 62 | | | none | 0 | 1.59 | x |
| 63 | | | 4,5-Dipiperidino-3-hydroxypyridazine | 0.05 | 0.63 | ○ |
| 64 | Red 227 (Acid Fuchsine D) | 0.0001 | 3-Hydroxy-4-piperidinopyridazine | 0.05 | 0.65 | ○ |
| 65 | Yellow 5 (Sunset Yellow FCF) | 0.0001 | 3-Hydroxy-5-piperidinopyridazine | 0.05 | 0.68 | ○ |
| 66 | | | 2-Hyroxy-4-methoxybenzophenone | 0.05 | 0.88 | Δ |
| 67 | | | 4-tert-Butyl-4'-methoxydibenzoylmethane | 0.05 | 0.80 | Δ |
| 68 | | | none | 0 | 3.77 | x |
| 69 | | | 3-Hydroxy-4-morpholinopyridazine | 0.05 | 0.80 | ○ |
| 70 | Red 106 (Acid red) | 0.00001 | 3-Hydroxy-5-morpholinopyridazine | 0.05 | 0.85 | ○ |
| 71 | Yellow 203 (Quinoline Yellow WS) | 0.0001 | 5-Bis(2-hydroxyethyl)amino-3-hydroxypyridazine | 0.05 | 0.85 | ○ |
| 72 | | | 2-Hydroxy-4-methoxybenzophenone | 0.05 | 1.11 | Δ |
| 73 | | | 4-tert-Butyl-4'-methoxydibenzoylmethane | 0.05 | 1.02 | Δ |
| 74 | | | none | 0 | 1.45 | x |
| 75 | | | 3-Hydroxy-6-morpholinopyridazine | 0.05 | 0.44 | ○ |
| 76 | Yellow 203 (Quinoline Yellow WS) | 0.0001 | 3,6-Bis(2-hydroxyethylamino)pyridazine | 0.05 | 0.47 | ○ |
| 77 | Yellow 5 (Sunset Yellow FCF) | 0.0001 | 3,6-Dimorpholinopyridazine | 0.05 | 0.40 | ○ |
| 78 | | | 2-Hydroxy-4-methoxybenzophenone | 0.05 | 0.52 | ○ |
| 79 | | | 4-tert-Butyl-4'-methoxydibenzoylmethane | 0.05 | 0.48 | ○ |
| 80 | | | none | 0 | 3.89 | x |
| 81 | | | 4,5-Dipiperidino-3-hydroxypyridazine | 0.05 | 1.11 | ○ |
| 82 | Red 213 (Rhodamine B) | 0.00001 | 3-Hydroxy-5-piperidinopyridazine | 0.05 | 1.01 | ○ |
| 83 | Blue 1 (Brilliant Blue FCF) | 0.00001 | 3-Hydroxy-5-morpholinopyridazine | 0.05 | 1.08 | ○ |
| 84 | | | 2-Hydroxy-4-methoxybenzophenone | 0.05 | 1.26 | Δ |
| 85 | | | 4-tert-Butyl-4'-methoxydibenzoylmethane | 0.05 | 1.17 | Δ |
| 86 | | | none | 0 | 3.04 | x |
| 87 | | | 3-Hydroxy-6-morpholinopyridazine | 0.05 | 0.52 | ○ |
| 88 | Red 401 (Violanin R) | 0.0001 | 3-Hydroxy-5-morpholinopyridazine | 0.05 | 0.44 | ○ |

TABLE 9-continued

| Test Example | Dye Compounds | Blend amount | Photostabilizer Compounds | Blend amount | Δ E | Daylight exposure (80 MJ) Appearance (visual determination) |
|---|---|---|---|---|---|---|
| 89 | Blue 1 (Brilliant Blue FCF) | 0.00001 | 4,5-Dipiperidino-3-hydroxypyridazine | 0.05 | 0.38 | ○ |
| 90 | | | 2-Hyroxy-4-methoxybenzophenone | 0.05 | 0.82 | Δ |
| 91 | | | 4-tert-Butyl-4'-methoxydibenzoylmethane | 0.05 | 0.93 | Δ |

Determination of appearance
○: no change;
Δ: almost no change;
x: change

The results shown in Tables 7 to 9 indicate that the color difference (ΔE) of the pyridazine derivative of the invention is extremely small, compared with the color difference of other photostabilizers. Further, the change of the appearance of the compositions is less. Therefore, it is indicated that the pyridazine derivative of the invention has excellent photostabilization effect on dyes.

Further, the photostabilization effects of the following formulations on individual pharmaceutical agents and the change of the appearance of the compositions were examined, by using the following assessment standards.

TEST EXAMPLES 92 TO 181

Formulations for Assessment of Stabilization Effect on Perfume

| Name of raw material | Blend amount (wt %) |
|---|---|
| Ion exchange water | to 100 |
| Brucine-modified alcohol | 5 |

-continued

| Name of raw material | Blend amount (wt %) |
|---|---|
| Glycerin | 5 |
| Dipropylene glycol | 5 |
| Polyoxyethylene-hydrogenated castor oil | 1 |
| Methylparaben | 0.2 |
| Lactic acid | 0.006 |
| Sodium lactate | 0.2 |
| Photostabilizer (described in Tables 10 to 12) | described in tables 10 to 12 |
| Perfume (described in Tables 10 to 12) | described in tables 10 to 12 |
| Total | 100 |

Each test sample was prepared for observation of the change of the odor of the test sample (determined by perfume coordinator) before and after daylight exposure (80 MJ).

The results are shown in Tables 10 to 12.

TABLE 10

| Test Example | Natural perfume Name | Photostabilizer Compounds | blend amount | daylight exposure (80 MJ) odor determination |
|---|---|---|---|---|
| 92 | Rose oil | none | 0 | x |
| 93 | | 4,5-Dipiperidino-3-hydroxypyridazine | 0.05 | ○ |
| 94 | | 3-Hydroxy-4-piperidinopyridazine | 0.05 | ○ |
| 95 | | 3-Hydroxy-5-piperidinopyridazine | 0.05 | ○ |
| 96 | | 2-Hydroxy-4-methoxybenzophenone | 0.05 | Δ |
| 97 | | 4-tert-Butyl-4'-methoxydibenzoylmethane | 0.05 | Δ |
| 98 | Jasmine oil | none | 0 | x |
| 99 | | 3-Hydroxy-4-morpholinopyridazine | 0.05 | ○ |
| 100 | | 3-Hydroxy-5-morpholinopyridazine | 0.05 | ○ |
| 101 | | 5-Bis(2-hydroxyethyl)amino-3-hydroxypyridazine | 0.05 | ○ |
| 102 | | 2-Hydroxy-4-methoxybenzophenone | 0.05 | Δ |
| 103 | | 4-tert-Butyl-4'-methoxydibenzoylmethane | 0.05 | Δ |
| 104 | Nelori oil | none | 0 | x |
| 105 | | 3-Hydroxy-6-morpholinopyridazine | 0.1 | ○ |
| 106 | | 3,6-Bis(2-hydroxyethylamino)pyridazine | 0.1 | ○ |
| 107 | | 3,6-Bimorpholinopyridazine | 0.1 | ○ |
| 108 | | 2-Hydroxy-4-methoxybenzophenone | 0.1 | Δ |
| 109 | | 4-tert-Butyl-4'-methoxydibenzoylmethane | 0.1 | Δ |
| 110 | Lavender oil | none | 0 | x |
| 111 | | 4,5-Dipiperidino-3-hydroxypyridazine | 0.1 | ○ |
| 112 | | 3-Hydroxy-5-piperidinopyridazine | 0.1 | ○ |
| 113 | | 3-Hydroxy-5-morpholinopyridazine | 0.1 | ○ |
| 114 | | 2-Hydroxy-4-methoxybenzophenone | 0.1 | Δ |
| 115 | | 4-tert-Butyl-4'-methoxydibenzoylmethane | 0.1 | Δ |
| 116 | Ylang ylang oil | none | 0 | x |
| 117 | | 3-Hydroxy-6-morpholinopyridazine | 0.2 | ○ |
| 118 | | 3-Hydroxy-5-morpholinopyridazine | 0.2 | ○ |
| 119 | | 4,5-Dipiperidino-3-hydroxypyridazine | 0.2 | ○ |

TABLE 10-continued

| Test Example | Natural perfume Name | Photostabilizer Compounds | blend amount | daylight exposure (80 MJ) odor determination |
|---|---|---|---|---|
| 120 | | 2-Hydroxy-4-methoxybenzophenone | 0.2 | Δ |
| 121 | | 4-tert-Butyl-4'-methoxydibenzoylmethane | 0.2 | Δ |

Determination of odor
○: no change;
Δ: almost no change;
x: change

TABLE 11

| Test Example | Synthetic perfume Name | Photostabilizer Compounds | blend amount | daylight exposure (80 MJ) odor determination |
|---|---|---|---|---|
| 122 | Limonene oil | none | 0 | x |
| 123 | | 3-Hydroxy-6-morpholinopyridazine | 0.05 | ○ |
| 124 | | 3,6-Bis(2-hydroxyethylamino)pyridazine | 0.05 | ○ |
| 125 | | 3,6-Dimorpholinopyridazine | 0.05 | ○ |
| 126 | | 2-Hydroxy-4-methoxybenzophenone | 0.05 | Δ |
| 127 | | 4-tert-Butyl-4'-methoxydibenzoylmethane | 0.05 | Δ |
| 128 | Linalool | none | 0 | x |
| 129 | | 3-Hydroxy-6-morpholinopyridazine | 0.05 | ○ |
| 130 | | 3-Hydroxy-5-morpholinopyridazine | 0.05 | ○ |
| 131 | | 4,5-Dipiperidino-3-hydroxypyridazine | 0.05 | ○ |
| 132 | | 2-Hydroxy-4-methoxybenzophenone | 0.05 | Δ |
| 133 | | 4-tert-Butyl-4'-methoxydibenzoylmethane | 0.05 | Δ |
| 134 | Citral | none | 0 | x |
| 135 | | 4,5-Dipiperidino-3-hydroxypyridazine | 0.1 | ○ |
| 136 | | 3-Hydroxy-5-piperidinopyridazine | 0.1 | ○ |
| 137 | | 3-Hydroxy-5-morpholinopyridazine | 0.1 | ○ |
| 138 | | 2-Hydroxy-4-methoxybenzophenone | 0.1 | Δ |
| 139 | | 4-tert-Butyl-4'-methoxydibenzoylmethane | 0.1 | Δ |
| 140 | Linalyl acetate | none | 0 | x |
| 141 | | 4,5-Dipiperidino-3-hydroxypyridazine | 0.1 | ○ |
| 142 | | 3-Hydroxy-5-piperidinopyridazine | 0.1 | ○ |
| 143 | | 3-Hydroxy-5-morpholinopyridazine | 0.1 | ○ |
| 144 | | 2-Hydroxy-4-methoxybenzophenone | 0.1 | Δ |
| 145 | | 4-tert-Butyl-4'-methoxydibenzoylmethane | 0.1 | Δ |
| 146 | Rose oxide | none | 0 | x |
| 147 | | 3-Hydroxy-4-morpholinopyridazine | 0.2 | ○ |
| 148 | | 3-Hydroxy-5-morpholinopyridazine | 0.2 | ○ |
| 149 | | 5-Bis(2-hydroxyethyl)amino-3-hydroxypyridazine | 0.2 | ○ |
| 150 | | 2-Hydroxy-4-methoxybenzophenone | 0.2 | Δ |
| 151 | | 4-tert-Butyl-4'-methoxydibenzoylmethane | 0.2 | Δ |

Determination of odor
○: no change;
Δ: almost no change;
x: change

TABLE 12

| Test Example | Base perfume designation | Photostabilizer designation | blend amount | Daylight exposure (80 MJ) odor determination |
|---|---|---|---|---|
| 152 | Rose | none | 0 | x |
| 153 | | 4,5-Dipiperidino-3-hydroxypyridazine | 0.05 | ○ |
| 154 | | 3-Hydroxy-4-piperidinopyridazine | 0.05 | ○ |
| 155 | | 3-Hydroxy-5-piperidinopyridazine | 0.05 | ○ |
| 156 | | 2-Hydroxy-4-methoxybenzophenone | 0.05 | Δ |
| 157 | | 4-tert-Butyl-4'-methoxybenzoylmethane | 0.05 | Δ |
| 158 | Muge | none | 0 | x |
| 159 | | 3-Hydroxy-4-morpholinopyridazine | 0.05 | ○ |
| 160 | | 3-Hydroxy-5-morpholinopyridazine | 0.05 | ○ |
| 161 | | 5-Bis(2-hydroxyethyl)amino-3-hydroxypyridazine | 0.05 | ○ |
| 162 | | 2-Hydroxy-4-methoxybenzophenone | 0.05 | Δ |
| 163 | | 4-tert-Butyl-4'-methoxybenzoylmethane | 0.05 | Δ |
| 164 | Woody | none | 0 | x |
| 165 | | 4,5-Dipiperidino-3-hydroxypyridazine | 0.1 | ○ |
| 166 | | 3-Hydroxy-4-piperidinopyridazine | 0.1 | ○ |
| 167 | | 3-Hydroxy-5-piperidinopyridazine | 0.1 | ○ |

TABLE 12-continued

| Test Example | Base perfume designation | Photostabilizer designation | blend amount | Daylight exposure (80 MJ) odor determination |
|---|---|---|---|---|
| 168 | | 2-Hydroxy-4-methoxybenzophenone | 0.1 | Δ |
| 169 | | 4-tert-Butyl-4'-methoxybenzoylmethane | 0.1 | Δ |
| 170 | Fruity | none | 0 | x |
| 171 | | 3-Hydroxy-4-morpholinopyridazine | 0.1 | ○ |
| 172 | | 3,6-Bis(2-hydorxyethylamino)pyridazine | 0.1 | ○ |
| 173 | | 3,6-Dimorpholinopyridazine | 0.1 | ○ |
| 174 | | 2-Hydroxy-4-methoxybenzophenone | 0.1 | Δ |
| 175 | | 4-tert-Butyl-4'-methoxybenzoylmethane | 0.1 | Δ |
| 176 | Spicy | none | 0 | x |
| 177 | | 3-Hydroxy-4-morpholinopyridazine | 0.2 | ○ |
| 178 | | 3-Hydroxy-5-morpholinopyridazine | 0.2 | ○ |
| 179 | | 4,5-Dipiperidino-3-hydroxypyridazine | 0.2 | ○ |
| 180 | | 2-Hydroxy-4-methoxybenzophenone | 0.2 | Δ |
| 181 | | 4-tert-Butyl-4'-methoxybenzoylmethane | 0.2 | Δ |

Determination of odor
○: no change;
Δ: almost no change;
x: change:

The results in tables 10 to 12 show that the change of the odor of the pyridazine derivative of the invention is far less, compared with other photostabilizers. Thus, it is indicated that the pyridazine derivative of the invention has better photostabilization effect on perfume.

Furthermore, the combination of the pyridazine derivative of the invention with sequestering agents has a synergistic effect on the photostabilization effect, taking in account that sequestering agents when used singly hardly have any photostabilization effect.

Then, the photostabilization effect on drugs and the change of the appearance of each composition were examined, by using the following formulations for assessment.

TEST EXAMPLES 182 TO 211
Assessment Formulations for Drug Stabilization Effect

| Name of raw material | Blend amount (wt %) |
|---|---|
| Ion exchange water | to 100 |
| Brucine-modified alcohol | 5 |
| Glycerin | 5 |
| Dipropylene glycol | 5 |
| Polyoxyethylene-hydrogenated castor oil | 1 |
| Methylparaben | 0.2 |
| Lactic acid | 0.006 |
| Sodium lactate | 0.2 |
| Photostabilizer (described in Table 13) | described in Table 13 |
| Drug (described in Table 13) | described in Table 13 |
| Total | 100 |

For observation of the change of the appearance of each test sample (determination based on visual observation) and the measurement of the remaining ratio by liquid chromatography before and after daylight exposure (80 MJ), the test sample was prepared. The results are shown in Table 13.

TABLE 13

| Test Example | Drug Compounds | blend amount | Photostabilizer Compounds | blend amount | Daylight exposure (80 MJ) Remaining ratio (%) | appearance (visual determination) |
|---|---|---|---|---|---|---|
| 182 | salicylic acid | 0.1 | none | 0 | 87.6 | x |
| 183 | | | 4,5-Dipiperidino-3-hydroxypyridazine | 0.05 | 99.6 | ○ |
| 184 | | | 3-Hydroxy-4-piperidinopyridazine | 0.05 | 98.4 | ○ |
| 185 | | | 3-Hydroxy-5-piperidinopyridazine | 0.05 | 98.5 | ○ |
| 186 | | | 2-Hydroxy-4-methoxybenzophenone | 0.05 | 98.2 | Δ |
| 187 | | | 4-tert-Butyl-4'-methoxybenzoylmethane | 0.05 | 97.2 | Δ |
| 188 | Dipotassium | 0.05 | none | 0 | 85.1 | x |
| 189 | glycyrrhizinate | | 3-Hydroxy-4-morpholinopyridazine | 0.05 | 99.2 | ○ |
| 190 | | | 3-Hydroxy-5-morpholinopyridazine | 0.05 | 98.9 | ○ |
| 191 | | | 3,6-Bis(2-hydroxyethylamino)pyridazine | 0.05 | 98.8 | ○ |
| 192 | | | 2-Hydroxy-4-methoxybenzophenone | 0.05 | 97.8 | Δ |
| 193 | | | 4-tert-Butyl-4'-methoxybenzoylmethane | 0.05 | 96.6 | Δ |
| 194 | dl-α-tocopherol | 0.01 | none | 0 | 69.0 | x |
| 195 | 2-L-ascorbic acid | | 4,5-Dipiperidino-3-hydroxypyridazine | 0.05 | 99.1 | ○ |
| 196 | phosphate diester | | 3-Hydroxy-5-piperidinopyridazine | 0.05 | 98.7 | ○ |

TABLE 13-continued

| | | | | | Daylight exposure (80 MJ) | |
| | Drug | | Photostabilizer | | | appearance |
| Test Example | Compounds | blend amount | Compounds | blend amount | Remaining ratio (%) | (visual determination) |
|---|---|---|---|---|---|---|
| 197 | potassium salt | | 3-Hydroxy-5-morpholinopyridazine | 0.05 | 98.0 | ○ |
| 198 | | | 2-Hydroxy-4-methoxybenzophenone | 0.05 | 95.4 | Δ |
| 199 | | | 4-tert-Butyl-4'-methoxybenzoylmethane | 0.05 | 94.5 | Δ |
| 200 | L-ascorbic acid | 2.0 | none | 0 | 84.7 | x |
| 201 | 2-glucoside | | 4,5-Dipiperidino-3-hydroxypyridazine | 0.05 | 99.3 | ○ |
| 202 | | | 3,6-Bis(2-hydroxyethylamino)pyridazine | 0.05 | 98.8 | ○ |
| 203 | | | 3,6-Dimorpholinopyridazine | 0.05 | 98.5 | ○ |
| 204 | | | 2-Hydroxy-4-methoxybenzophenone | 0.05 | 97.8 | Δ |
| 205 | | | 4-tert-Butyl-4'-methoxybenzoylmethane | 0.05 | 97.0 | Δ |
| 206 | dibutylhydroxytoluene | 0.01 | none | 0 | 48.0 | x |
| 207 | | | 3-Hydroxy-6-morpholinopyridazine | 0.05 | 98.0 | ○ |
| 208 | | | 3-Hydroxy-5-morpholinopyridazine | 0.05 | 98.8 | ○ |
| 209 | | | 4,5-Dipiperidino-3-hydroxypyridazine | 0.05 | 99.0 | ○ |
| 210 | | | 2-Hydroxy-4-methoxybenzophenone | 0.05 | 95.2 | Δ |
| 211 | | | 4-tert-Butyl-4'-methoxydibenzoylmethane | 0.05 | 95.2 | Δ |

Determination of appearance
○: no change;
Δ: almost no change;
x: change

The results in table 13 indicate that the remaining ratio of drugs via the pyridazine derivative of the invention is far higher, compared with other photostabilizers. Furthermore, it is indicated that the change of the appearance of the compositions is less. Thus, the pyridazine derivative of the invention has excellent photostabilization effect on drugs. The present inventors made attempts to improve the photostabilization effect by using a combination of the photostabilizer with sequestering agents.

First, the inventors examined the photostabilization effect of dyes and the change of the appearance of each composition, using the following assessment formulations.

TEST EXAMPLES 212 TO 275
Assessment Formulation of Dye Stabilization Effect (in Blend with Sequestering Agents)
(Blended with Sequestering Agents)

| Name of raw material | Blend amount (wt %) |
|---|---|
| Ion exchange water | to 100 |
| Brucine-modified alcohol | 5 |
| Glycerin | 5 |
| Dipropylene glycol | 5 |
| Polyoxyethylene-hydrogenated castor oil | 1 |
| Methylparaben | 0.2 |

| Name of raw material | Blend amount (wt %) |
|---|---|
| Lactic acid | 0.006 |
| Sodium lactate | 0.2 |
| sequestering agent (described in Tables 14 to 15) | described in Tables 14 to 15 |
| Photostabilizer (described in Tables 14 to 15) | described in Tables 14 to 15 |
| Dye (described in Tables 14 to 15) | Described in Tables 14 to 15 |
| Total | 100 |

Each test sample was prepared for observation of the change of the appearance of each test sample (determined visually) and measurement of the color difference (ΔE) before and after daylight exposure (80 MJ).

With a spectrophotometer, the color was measured on the Lab coordinate system, to calculate the color difference on the basis of the color before daylight exposure. More specifically, the color difference (ΔE) was calculated on the basis of the measured values ($L_1$, $a_1$, $b_1$) before daylight exposure.

$$\Delta E = [(L_2-L_1)^2 + (a_2-a_1)^2 + (b_2-b_1)^2]^{1/2}$$

The results are shown in Tables 14 to 15.

TABLE 14

| | Dye | | Sequestering agent | | Photostabilizer | | Daylight exposure (80 MJ) | |
| Test Example | Name | blend amount | Name | blend amount | Compounds | Blend amount | Δ E | Appearance (visual determination) |
|---|---|---|---|---|---|---|---|---|
| 212 | | 0.0001 | — | 0 | | 0 | 1.45 | x |
| 213 | | | | | | 0.01 | 0.98 | Δ |
| 214 | | | ethylenediaminetetraacetate | 0.02 | | 0 | 1.40 | x |
| 215 | Red 227 | | trisodium | | 4,5-Dipiperidino- | 0.01 | 0.72 | ○ |

TABLE 14-continued

| | Dye | | Sequestering agent | | Photostabilizer | | Daylight exposure (80 MJ) | |
|---|---|---|---|---|---|---|---|---|
| Test Example | Name | blend amount | Name | blend amount | Compounds | Blend amount | Δ E | Appearance (visual determination) |
| 216 | (Acid Fuchsine D) | | sodium metaphosphate | 0.02 | 3-hydroxypyridazine | 0 | 1.37 | x |
| 217 | | | | | | 0.01 | 0.61 | ○ |
| 218 | | | ethylenediaminehydroxyethyl trisodium triacetate | 0.02 | | 0 | 1.43 | x |
| 219 | | | | | | 0.01 | 0.52 | ○ |
| 220 | | 0.0001 | — | 0 | 3-Hydroxy-5-morpholinopyridazine | 0 | 1.83 | x |
| 221 | | | | | | 0.01 | 0.61 | ○ |
| 222 | | | ethylenediaminetetraacetate trisodium | 0.03 | | 0 | 1.72 | x |
| 223 | Yellow 5 | | | | | 0.01 | 0.52 | ○ |
| 224 | (Sunset Yellow FCF) | | sodium metaphosphate | 0.03 | | 0 | 1.68 | x |
| 225 | | | | | | 0.01 | 0.55 | ○ |
| 226 | | | sodium polyphosphate | 0.03 | | 0 | 1.70 | x |
| 227 | | | | | | 0.01 | 0.46 | ○ |
| 228 | | 0.001 | — | 0 | 3-Hydroxy-5-piperidinopyridazine | 0 | 8.92 | x |
| 229 | | | | | | 0.02 | 1.74 | Δ |
| 230 | | | ethylenediaminetetraacetate trisodium | 0.05 | | 0 | 8.32 | x |
| 231 | Blue 1 | | | | | 0.02 | 0.78 | ○ |
| 232 | Brilliant Blue FCF) | | sodium metaphosphate | 0.05 | | 0 | 7.78 | x |
| 233 | | | | | | 0.02 | 0.88 | ○ |
| 234 | | | ethylenediaminehydroxyethyl trisodium triacetate | 0.05 | | 0 | 7.63 | x |
| 235 | | | | | | 0.02 | 0.54 | ○ |
| 236 | | 0.001 | — | 0 | 3-Hydroxy-6-morpholinopyridazine | 0 | 2.12 | x |
| 237 | | | | | | 0.02 | 0.75 | ○ |
| 238 | | | ethylenediaminetetraacetate trisodium | 0.1 | | 0 | 1.75 | x |
| 239 | Green 3 | | | | | 0.02 | 0.32 | ○ |
| 240 | (Fast Green FCF) | | sodium metaphosphate | 0.1 | | 0 | 1.77 | x |
| 241 | | | | | | 0.02 | 0.36 | ○ |
| 242 | | | sodium polyphosphate | 0.1 | | 0 | 1.75 | x |
| 243 | | | | | | 0.02 | 0.52 | ○ |

Determination of appearance
○: no change;
Δ: almost no change;
x: change

TABLE 15

| | Dyes | | Sequestering agent | | Photostabilizer | | Daylight exposure (80 MJ) | |
|---|---|---|---|---|---|---|---|---|
| Test Example | Name | blend amount | Name | blend amount | Compounds | Blend amount | Δ E | Appearance (visual determination) |
| 244 | Red 227 | 0.0001 | — | 0 | 4,5-Dipipendino-3-hydroxypyridazine | 0 | 1.59 | x |
| 245 | (Acid Fuchsine D) | | | | | 0.01 | 1.12 | Δ |
| 246 | Yellow 5 | 0.0001 | ethylenediaminetetraacetate trisodium | 0.02 | | 0 | 1.55 | x |
| 247 | (Sunset Yellow FCF) | | | | | 0.01 | 0.68 | ○ |
| 248 | Red 227 | 0.0001 | — | 0 | 3-Hydroxy-5-morpholinopyridazine | 0 | 3.05 | x |
| 249 | (Acid Fuchsine D) | | | | | 0.01 | 1.68 | Δ |
| 250 | Yellow 203 | 0.0001 | sodium metaphosphate | 0.02 | | 0 | 3.01 | x |
| 251 | (Quinoline Yellow WS) | | | | | 0.01 | 0.98 | ○ |
| 252 | Red 106 | 0.00001 | — | 0 | 3-Hydroxy-5-piperidino-pyridazine | 0 | 3.77 | x |
| 253 | (Acid Red) | | | | | 0.01 | 1.08 | ○ |
| 254 | Yellow 203 | 0.0001 | ethylenediaminehydroxyethyl trisodium triacetate | 0.02 | | 0 | 3.56 | x |
| 255 | (Quinoline Yellow WS) | | | | | 0.01 | 0.72 | ○ |
| 256 | Red 106 | 0.00001 | — | 0 | 3-Hydroxy-6-morpholino-pyridazine | 0 | 4.45 | x |
| 257 | (Acid Red) | | | | | 0.01 | 1.38 | Δ |
| 258 | Yellow 5 | 0.0001 | ethylenediaminetetraacetate trisodium | 0.02 | | 0 | 4.26 | x |
| 259 | (Sunset Yellow FCF) | | | | | 0.01 | 0.92 | ○ |
| 260 | Yellow 203 | 0.0001 | — | 0 | 3,6-Bis(2-hydroxyethylamino) pyridazine | 0 | 1.45 | x |
| 261 | (Quinoline Yellow WS) | | | | | 0.02 | 0.88 | ○ |

TABLE 15-continued

| Test Example | Dyes Name | Dyes blend amount | Sequestering agent Name | Sequestering agent blend amount | Photostabilizer Compounds | Photostabilizer Blend amount | Daylight exposure (80 MJ) ΔE | Appearance (visual determination) |
|---|---|---|---|---|---|---|---|---|
| 262 | Yellow 5 | 0.0001 | sodium metaphosphate | 0.01 | | 0 | 1.44 | x |
| 263 | (Sunset Yellow FCF) | | | | | 0.02 | 0.55 | ○ |
| 264 | Red 213 | 0.00001 | — | 0 | 3,6-Dimorpholinopyridazine | 0 | 3.89 | x |
| 265 | (Rhodamine B) | | | | | 0.02 | 1.98 | Δ |
| 266 | Blue 1 | 0.00001 | ethylenediaminehydroxyethyl trisodium triacetate | 0.03 | | 0 | 3.85 | x |
| 267 | Brilliant Blue FCF) | | | | | 0.02 | 1.32 | ○ |
| 268 | Red 401 | 0.0001 | — | 0 | 3-Hydroxy-4-morpholino-pyridazine | 0 | 3.04 | x |
| 269 | 401 (Violanin R) | | | | | 0.02 | 1.34 | ○ |
| 270 | Blue 1 | 0.00001 | ethylenediaminetetraacetate trisodium | 0.03 | | 0 | 3.02 | x |
| 271 | Brilliant Blue FCF) | | | | | 0.02 | 0.91 | ○ |
| 272 | Red 401 | 0.0001 | — | 0 | | 0 | 4.54 | x |
| 273 | 401 (Violanin R) | | | | 4,5-Dipiperidino-33-hydroxy pyridazine | 0.02 | 1.52 | Δ |
| 274 | Green 3 | 0.00001 | sodium metaphosphate | 0.03 | | 0 | 4.23 | x |
| 275 | (Fast Green FCF) | | | | | 0.02 | 0.77 | ○ |

Determination of appearance
○ no change,
Δ: almost no change,
x: change

The results in tables 14 and 15 indicate that the color difference (ΔE) of the pyridazine derivative of the invention in combination with sequestering agents is small, compared with no combination with sequestering agents. It is also indicated that the change of the appearance of the composition is less. Thus, the pyridazine derivative of the invention has more excellent photostabilization effect on dyes, when used in combination with sequestering agents.

Taking into account that sequestering agents hardly have photostabilization effect, furthermore, the combination of the pyridazine derivative of the invention in combination with sequestering agents has a synergistic effect on the photostabilization effect.

The photostabilization effect of the combination with sequestering agents on each perfume was then examined, by using the following formulation for assessment.

TEST EXAMPLES 276 TO 371

Formulations for Assessment of Stabilization Effect on Perfume (Blended with Sequestering Agents)

| Name of raw material | Blend amount (wt %) |
|---|---|
| Ion exchange water | to 100 |
| Brucine-modified alcohol | 5 |
| Glycerin | 5 |
| Dipropylene glycol | 5 |
| Polyoxyethylene-hydrogenated castor oil | 1 |
| Methylparaben | 0.2 |
| Lactic acid | 0.006 |
| Sodium lactate | 0.2 |
| sequestering agent (described in Tables 16 to 18) | described in Tables 16 to 18 |
| Photostabilizer (described in Tables 16 to 18) | described in Tables 16 to 18 |
| Perfume (described in Tables 16 to 18) | 0.03 |
| Total | 100 |

Each test sample was prepared for observation of the change of the odor of each test sample (determined by perfume coordinator) before and after daylight exposure (80 MJ).

The results are shown in Tables 16 to 18.

TABLE 16

| Test Example | Natural perfume Name | Sequestering agent Name | Sequestering agent blend amount | Photostabilizer Compounds | Photostabilizer blend amount | daylight exposure (80 MJ) odor determination |
|---|---|---|---|---|---|---|
| 276 | Rose oil | — | 0 | | 0 | x |
| 277 | | | | 4,5-Dipiperidino-3-hydroxypyridazine | 0.02 | Δ |
| 278 | | ethylenediaminetetraacetate | 0.03 | | 0 | x |

TABLE 16-continued

| Test Example | Natural perfume Name | Sequestering agent Name | blend amount | Photostabilizer Compounds | blend amount | daylight exposure (80 MJ) odor determination |
|---|---|---|---|---|---|---|
| 279 | | trisodium | | | 0.02 | ○ |
| 280 | Jasmine oil | — | 0 | 3-Hydroxy-5-morpholinopyridazine | 0 | x |
| 281 | | | | | 0.02 | Δ |
| 282 | | sodium metaphosphate | 0.03 | | 0 | x |
| 283 | | | | | 0.02 | ○ |
| 284 | Lavender oil | — | 0 | 3-Hydroxy-5-piperidinopyridazine | 0 | x |
| 285 | | | | | 0.02 | Δ |
| 286 | | ethylenediaminehydroxyethyl | 0.03 | | 0 | x |
| 287 | | triacetate trisodium | | | 0.02 | ○ |
| 288 | Peppermint oil | — | 0 | 3-Hydroxy-6-morpholinopyridazine | 0 | x |
| 289 | | | | | 0.01 | Δ |
| 290 | | ethylenediaminetetraacetate | 0.03 | | 0 | x |
| 291 | | trisodium | | | 0.01 | ○ |
| 292 | Orange oil | — | 0 | | 0 | x |
| 293 | | | | 3,6-Bis(2-hydroxyethylamino)pyridazine | 0.05 | Δ |
| 294 | | sodium metaphosphate | 0.03 | | 0 | x |
| 295 | | | | | 0.05 | ○ |
| 296 | Ylang ylang oil | — | 0 | 3,6-Dimorpholinopyridazine | 0 | x |
| 297 | | | | | 0.02 | Δ |
| 298 | | ethylenediaminehydroxyethyl | 0.03 | | 0 | x |
| 299 | | triacetate trisodium | | | 0.02 | ○ |
| 300 | Bergamot oil | — | 0 | 3-Hydroxy-4-morpholinopyridazine | 0 | x |
| 301 | | | | | 0.05 | Δ |
| 302 | | ethylenediaminetetraacetate | 0.03 | | 0 | x |
| 303 | | trisodium | | | 0.05 | ○ |
| 304 | Musk oil | — | 0 | | 0 | x |
| 305 | | | | 4,5-Dipiperidino-3-hydroxypyridazine | 0.1 | Δ |
| 306 | | sodium metaphosphate | 0.03 | | 0 | x |
| 307 | | | | | 0.1 | ○ |

Determination of odor:
○: no change;
Δ: almost no change;
x: change

TABLE 17

| Test Example | Synthetic perfume designation | Sequestering agent Name | blend amount | Photostabilizer Compounds | blend amount | daylight exposure (80 MJ) odor determination |
|---|---|---|---|---|---|---|
| 308 | Limonene | — | 0 | | 0 | x |
| 309 | | | | 4,5-Dipiperidino-3-hydroxypyridazine | 0.02 | Δ |
| 310 | | ethylenediaminehydroxyethyl | 0.03 | | 0 | x |
| 311 | | triacetate sodium | | | 0.02 | ○ |
| 312 | cis-3-Hexenol | — | 0 | 3-Hydroxy-5-morpholinopyridazine | 0 | x |
| 313 | | | | | 0.02 | Δ |
| 314 | | ethylenediaminetetraacetate | 0.03 | | 0 | x |
| 315 | | trisodium | | | 0.02 | ○ |
| 316 | Citral | — | 0 | 3-Hydroxy-5-piperidinopyridazine | 0 | x |
| 317 | | | | | 0.01 | Δ |
| 318 | | ethylenediaminehydroxyethyl | 0.03 | | 0 | x |
| 319 | | triacetate sodium | | | 0.01 | ○ |
| 320 | β-Ionone | — | 0 | 3-Hydroxy-6-morpholinopyridazine | 0 | x |
| 321 | | | | | 0.01 | Δ |
| 322 | | ethylenediaminetetraacetate | 0.03 | | 0 | x |
| 323 | | trisodium | | | 0.01 | ○ |
| 324 | Auranthiol | — | 0 | | 0 | x |
| 325 | | | | 3,6-Bis(2-hydroxyethylamino) pyridazine | 0.05 | Δ |
| 326 | | sodium metaphosphate | 0.03 | | 0 | x |
| 327 | | | | | 0.05 | ○ |
| 328 | Benzyl benzoate | — | 0 | 3,6-Dimorpholinopyridazine | 0 | x |
| 329 | | | | | 0.02 | Δ |
| 330 | | ethylenediaminehydroxyethyl | 0.03 | | 0 | x |
| 331 | | triacetate sodium | | | 0.02 | ○ |
| 332 | Rose oxide | — | 0 | 3-Hydroxy-4-morpholinopyridazine | 0 | x |
| 333 | | | | | 0.05 | Δ |
| 334 | | ethylenediaminetetraacetate | 0.03 | | 0 | x |
| 335 | | trisodium | | | 0.05 | ○ |

TABLE 17-continued

| Test Example | Synthetic perfume designation | Sequestering agent Name | blend amount | Photostabilizer Compounds | blend amount | daylight exposure (80 MJ) odor determination |
|---|---|---|---|---|---|---|
| 336 | Lilial | — | 0 | | 0 | x |
| 337 | | | | 4,5-Dipiperidino-3-hydroxypyridazine | 0.1 | Δ |
| 338 | | sodium metaphosphate | 0.03 | | 0 | x |
| 339 | | | | | 0.1 | ○ |

Determination of odor:

○: no change;

Δ: almost no change;

x: change

TABLE 18

| Test Example | Base perfume Name | Sequestering agent Name | blend amount | Photostabilizer Compounds | blend amount | daylight exposure (80 MJ) odor determination |
|---|---|---|---|---|---|---|
| 340 | Rose | — | 0 | | 0 | x |
| 341 | | | | 4,5-Dipiperidino-3-hydroxypyridazine | 0.02 | Δ |
| 342 | | ethylenediaminehydroxyethyl triacetate trisodium | 0.03 | | 0 | x |
| 343 | | | | | 0.02 | ○ |
| 344 | Jasmine | — | 0 | 3-Hydroxy-5-morpholinopyridazine | 0 | x |
| 345 | | | | | 0.02 | Δ |
| 346 | | ethylenediaminetetraacetate trisodium | 0.03 | | 0 | x |
| 347 | | | | | 0.02 | ○ |
| 348 | Muge | — | 0 | 3-Hydroxy-5-piperidinopyridazine | 0 | x |
| 349 | | | | | 0.02 | Δ |
| 350 | | sodium metaphosphate | 0.03 | | 0 | x |
| 351 | | | | | 0.02 | ○ |
| 352 | Green | — | 0 | 3-Hydroxy-6-morpholinopyridazine | 0 | x |
| 353 | | | | | 0.01 | Δ |
| 354 | | ethylenediaminehydroxyethyl triacetate trisodium | 0.03 | | 0 | x |
| 355 | | | | | 0.01 | ○ |
| 356 | Oriental | — | 0 | | 0 | x |
| 357 | | | | 3,6-Bis(2-hydroxyethylamino) pyridazine | 0.01 | Δ |
| 358 | | ethylenediaminetetraacetate trisodium | 0.03 | | 0 | x |
| 359 | | | | | 0.01 | ○ |
| 360 | Fruity | — | 0 | 3,6-Dimorpholinopyridazine | 0 | x |
| 361 | | | | | 0.03 | Δ |
| 362 | | sodium metaphosphate | 0.03 | | 0 | x |
| 363 | | | | | 0.03 | ○ |
| 364 | Aldehyde | — | 0 | 3-Hydroxy-4-morpholinopyridazine | 0 | x |
| 365 | | | | | 0.05 | Δ |
| 366 | | ethylenediaminehydroxyethyl triacetate trisodium | 0.03 | | 0 | x |
| 367 | | | | | 0.05 | ○ |
| 368 | Animal | — | 0 | | 0 | x |
| 369 | | | | 4,5-Dipiperidino-3-hydroxypyridazine | 0.1 | Δ |
| 370 | | ethylenediaminetetraacetate trisodium | 0.03 | | 0 | x |
| 371 | | | | | 0.1 | ○ |

Determination of odor:

○: no change;

Δ: almost no change;

x: change

The results in tables 16 to 18 show that the change of odor in case of the combination of the pyridazine derivative of the invention with sequestering agents is less, compared with the case without any combination with sequestering agents. Thus, it is indicated that the pyridazine derivative of the invention has better photostabilization effect on perfume when the pyridazine derivative is used in combination with sequestering agents.

Furthermore, the combination of the pyridazine derivative of the invention with sequestering agents has a synergistic effect on the photostabilization effect, taking into account that sequestering agents when used singly hardly have any photostabilization effect.

Then, the photostabilization effect of the pyridazine derivative in combination with sequestering agents on each drug and the change of the appearance of each composition were examined, by using the following formulation for assessment.

TEST EXAMPLES 372 TO 391
Formulations for Assessment of Dye Stabilization Effect (Blended with Sequestering Agent)

| Name of raw material | Blend amount (wt %) |
| --- | --- |
| Ion exchange water | to 100 |
| Brucine-modified alcohol | 5 |
| Glycerin | 5 |
| Dipropylene glycol | 5 |
| Polyoxyethylene-hydrogenated castor oil | 1 |
| Methylparaben | 0.2 |
| Lactic acid | 0.006 |
| Sodium lactate | 0.2 |
| Photostabilizer (described in Table 19) | Described in Table 19 |
| Drug (described in Table 19) | Described in Table 19 |
| Total | 100 |

For observation of the change of the appearance of each test sample (determination based on visual observation) and the measurement of the remaining ratio by liquid chromatography before and after daylight exposure (80 MJ), the test sample was prepared.

TABLE 19

| | | | | | | | Daylight exposure (80 MJ) | |
| --- | --- | --- | --- | --- | --- | --- | --- | --- |
| | Drug | | Sequestering agent | | Photostabilizer | | | Appearance |
| Test Example | Compounds | blend amount | Name | blend amount | Compounds | Blend amount | remaining ratio (%) | (visual determination) |
| 372 | Salicylic acid | 0.1 | — | 0 | | 0 | 87.6 | x |
| 373 | | | | | 4,5-Dipiperidino-3-hydroxypyridazine | 0.03 | 99.1 | Δ |
| 374 | | | ethylenediamine tetraacetate trisodium | 0.03 | | 0 | 88.0 | x |
| 375 | | | | | | 0.03 | 99.8 | ○ |
| 376 | | 0.05 | — | 0 | 3-Hydroxy-5-morpholinopyridazine | 0 | 85.1 | x |
| 377 | Glycyrrhizinic acid dipotassium | | | | | 0.03 | 96.9 | ○ |
| 378 | | | sodium metaphosphate | 0.03 | | 0 | 85.8 | x |
| 379 | | | | | | 0.03 | 100.1 | ○ |
| 380 | dl-α-tocopherol 2-L-ascorbic acid phosphate diester potassium salt | 0.01 | — | 0 | 3-Hydroxy-5-piperidinopyridazine | 0 | 69.0 | x |
| 381 | | | | | | 0.03 | 98.2 | Δ |
| 382 | | | ethylenediamine-hydroxyethyl Triacetate trisodium | 0.03 | | 0 | 70.1 | x |
| 383 | | | | | | 0.03 | 99.4 | ○ |
| 384 | | 2.0 | — | 0 | 3-Hydroxy-6-morpholinopyridazine | 0 | 84.7 | x |
| 385 | L-ascorbic acid 2-glucoside | | | | | 0.03 | 97.9 | ○ |
| 386 | | | sodium metaphosphate | 0.03 | | 0 | 85.2 | x |
| 387 | | | | | | 0.03 | 99.2 | ○ |
| 388 | | 0.01 | — | 0 | 3,6-Dimorpholinopyridazine | 0 | 48.0 | x |
| 389 | dibutylhydroxy toluene | | | | | 0.03 | 95.2 | Δ |
| 390 | | | sodium metaphosphate | 0.03 | | 0 | 54.7 | x |
| 391 | | | | | | 0.03 | 98.8 | ○ |

Determination of appearance
○: no change;
Δ: almost no change;
x: change

The results shown in table 19 indicate that the remaining ratio of a pharmaceutical agent in case of the combination of the pyridazine derivative of the invention with sequestering agents is high, compared with the case without any combination with sequestering agents and additionally that the change of the appearance of each composition is less. Therefore, the pyridazine derivative of the invention in combination with sequestering agents has excellent photostabilization effect.

Further, the combination of the pyridazine derivative of the invention with sequestering agents has a synergistic effect on the photostabilization effect, taking into account that sequestering agents when used singly hardly have any photostabilization effect.

DESCRIPTION OF THE PREFERRED EMBODIMENTS

EXAMPLES

External preparations for skin in accordance with the invention is described below. However, the invention is not limited to these examples. Herein, all the blend amounts are expressed in wt %.

Example 1

Skin Lotion

| Alcohol phase | |
| --- | --- |
| Ethanol | 10.0 |
| Oleyl alcohol | 0.1 |
| POE(20) sorbitan monolaurate ester | 0.5 |
| POE(15) lauryl ether | 0.5 |
| 4,5-Dipiperidino-3-hydroxypyridazine | 5.0 |
| Preservative | appropriate amount |
| Perfume | appropriate amount |
| Aqueous phase | |
| 1,3-Butylene glycol | 6.0 |
| Glycerin | 4.0 |
| Ion exchange water | qs |

Production Process

The aqueous phase and the alcohol phase were separately prepared and were then mixed together.

Example 2

Skin Lotion

| Alcohol phase | |
| --- | --- |
| Ethanol | 10.0 |
| POE(20) oleyl ether | 0.5 |
| Preservative | appropriate amount |
| Perfume | appropriate amount |
| Aqueous phase | |
| Dipropylene glycol | 6.0 |
| Sorbit | 4.0 |
| PEG 1500 | 5.0 |
| 4,5-Dipiperidino-3-hydroxypyridazine hydrochloride salt | 20.0 |
| Methyl cellulose | 0.2 |
| Quince seed | 0.1 |
| Ion exchange water | qs |

Production Process

Methyl cellulose and Quince seed were mixed with a part of ion exchange water. The resulting mixture was agitated, to prepare a viscous solution. The remaining ion exchange water and other components of the aqueous phase were mixed and dissolved together, to which was added the viscous solution to prepare a homogenous aqueous phase. After the alcohol phase was prepared and added to the aqueous phase, the resulting mixture was mixed together.

Example 3

Cream

| | |
| --- | --- |
| Stearic acid | 5.0 |
| Stearyl alcohol | 4.0 |
| Isopropyl myristate | 18.0 |
| Glycerin monostearate ester | 3.0 |
| Propylene glycol | 10.0 |
| 3-Hydroxy-5-morpholinopyridazine | 20.0 |
| Potassium hydroxide | 0.2 |
| Sodium hydrogen sulfite | 0.01 |
| Preservative | appropriate amount |
| Perfume | appropriate amount |
| Ion exchange water | qs |

Production Process

Propylene glycol and potassium hydroxide were added to and dissolved in ion exchange water, and the resulting mixture was heated and retained at 70° C. (aqueous phase). Other components were mixed into the mixture, for melting under heating. The resulting mixture was retained at 70° C. (oil phase). The oil phase was gradually added to the aqueous phase, for preliminary emulsification and homogenous emulsification with a homomixer. Under sufficient agitation, the resulting emulsion was cooled to 30° C.

Example 4

Cream

| | |
| --- | --- |
| Stearic acid | 6.0 |
| Sorbitan monostearate ester | 2.0 |
| POE(20) sorbitan monostearate ester | 1.5 |
| Propylene glycol | 10.0 |
| 3-Hydroxy-5-piperidinopyridazine | 1.0 |
| Glycerin trioctanoate | 10.0 |
| Squalene | 5.0 |
| Sodium hydrogen sulfite | 0.01 |
| Ethylparaben | 0.3 |
| Perfume | appropriate amount |
| Ion exchange water | qs |

Production Process

Propylene glycol and 3-hydroxy-5-piperidinopyridazine were added to and dissolved in ion exchange water, and the resulting mixture was heated and retained at 70° C. (aqueous phase). Other components were mixed into the mixture, for melting under heating. The resulting mixture was retained at 70° C. (oil phase). The oil phase was gradually added to the aqueous phase, for preliminary emulsification and homogenous emulsification with a homomixer. Under sufficient agitation, the resulting emulsion was cooled to 30° C.

Example 5

Emulsion

| | |
| --- | --- |
| Stearic acid | 2.5 |
| Cetyl alcohol | 1.5 |
| Petrolatum | 10.0 |
| POE(10) monooleate ester | 2.0 |
| PEG 1500 | 3.0 |
| Triethanol amine | 1.0 |
| 3-Hydroxy-6-morpholinopyridazine | 10.0 |
| Sodium hydrogen sulfite | 0.01 |
| Ethylparaben | 0.3 |
| Carboxylvinyl polymer | 0.05 |
| Preservative | appropriate amount |
| Ion exchange water | qs |

Production Process

Carboxyvinyl polymer was dissolved in a small amount of ion exchange water (A phase). PEG 1500, 3-hydroxy-6-morpholinopyridazine and triethanol amine were added to the remaining part of ion exchange water, and the resulting mixture was dissolved together under heating and was then retained at 70° C. (Aqueous phase). Other components were mixed into the mixture, for melting under heating. The resulting mixture was retained at 70° C. (oil phase). The oil phase was gradually added to the aqueous phase, for preliminary emulsification. Then, the A phase was added to the resulting emulsion, which was then homogenously emulsified with a homomixer. Under sufficient agitation, the resulting emulsion was cooled to 30° C.

Example 6

Gel

| | |
|---|---|
| 95% Ethanol | 10.0 |
| Dipropylene glycol | 15.0 |
| POE(50) oleyl ether | 2.0 |
| Carboxyvinyl polymer | 1.0 |
| Sodium hydroxide | 0.15 |
| 3,6-Dimorpholinopyridazine | 2.0 |
| Methylparaben | 0.2 |
| Perfume | appropriate amount |
| Ion exchange water | qs |

Production Process

Carboxyvinyl polymer was homogenously dissolved in ion exchange water (A phase). 3,6-Dimorpholinopyridazine and POE(50) oleyl ether were dissolved in 95% ethanol, and the resulting solution was added to the A phase. After addition of the ingredients except for sodium hydroxide, sodium hydroxide was added for neutralization and thickening.

Example 7

Beauty Lotion

| | |
|---|---|
| A phase | |
| 95% Ethanol | 10.0 |
| POE(20) octyldodecanol | 1.0 |
| Methyl paraben | 0.15 |
| Pantothenyl ethyl ether | 0.1 |
| B phase | |
| Potassium hydroxide | 0.1 |
| C phase | |
| Glycerin | 5.0 |
| Dipropylene glycol | 10.0 |
| Sodium hydrogen sulfite | 0.03 |
| Carboxyvinyl polymer | 0.2 |
| 3-Hydroxy-4-piperidinopyridazine | 0.1 |
| Ion exchange water | qs |

Production Process

The A phase and the C phase were separately dissolved. Then, the resulting A phase was added to the resulting C phase for solubilization. Subsequently, the B phase was added to the mixture for mixing.

Example 8

Pack

| | |
|---|---|
| A phase | |
| Dipropylene glycol | 5.0 |
| POE(60) hydrogenated castor oil | 5.0 |
| B phase | |
| Olive oil | 5.0 |
| Tocopherol acetate | 0.2 |
| Ethylparaben | 0.2 |
| Perfume | 0.2 |
| C phase | |
| 5-Bis(2-hydroxyethyl)amino-3-hydroxypyridazine | 3.0 |
| Sodium hydrogen sulfite | 0.03 |
| Polyvinyl alcohol (saponification degree of 90; polymerization degree of 2000) | 13.0 |
| Ethanol | 7.0 |
| Ion exchange water | qs |

Production Process

The A phase, the B phase and the C phase were separately dissolved homogenously. Then, the resulting B phase was added to the resulting A phase, for solubilization. Then, the resulting mixture was added to the C phase for mixing.

All the Examples 1 to 7 had ultraviolet prevention effects. Furthermore, totally no skin trouble was observed in Examples 1 to 8.

Example 9

Emulsion

| | |
|---|---|
| Oil phase | |
| Stearyl alcohol | 1.5 |
| Squalene | 2.0 |
| Petrolatum | 2.5 |
| Odorless liquid lanolin | 1.5 |
| Evening primrose oil | 2.0 |
| Isopropyl myristate | 5.0 |
| Glycerin monooleate | 2.0 |
| POE(60) - hydrogenated castor oil | 2.0 |
| Tocopherol acetate | 0.05 |
| Ethylparaben | 0.2 |
| Butylparaben | 0.1 |
| Perfume | appropriate volume |
| Aqueous phase | |
| 3,6-Bis(2-hydroxyethylamino)pyridazine | 1.0 |
| 4,5-Dipiperidino-3-hydroxypyridazine | 1.0 |
| Sodium hydrogen sulfite | 0.01 |
| Glycerin | 5.0 |
| Sodium hyaluronate | 0.01 |
| Carboxyvinyl polymer | 0.2 |
| Potassium hydroxide | 0.2 |
| Ion exchange water | qs |

Production Process

The oil phase and the aqueous phase were separately dissolved at 70° C. Then, the resulting oil phase was added to the resulting aqueous phase, for emulsification with an emulsion machine. Then, the resulting mixture was cooled to 30° C. with a heat exchange machine.

The emulsion of the Example 9 had an excellent ultraviolet prevention effect alike, totally without any skin trouble.

Example 10

Solid Powdery Foundation

| | | |
|---|---|---|
| 1. | Talc | 15.0 |
| 2. | Sericite | 10.0 |
| 3. | Spherical nylon powder | 10.0 |
| 4. | Porous silicic anhydride powder | 15.0 |
| 5. | Boron nitride | 5.0 |
| 6. | Titanium dioxide | 5.0 |
| 7. | Iron oxide | 3.0 |
| 8. | Zinc stearate | 5.0 |
| 9. | 3-Hydroxy-5-morpholinopyridazine | 5.0 |
| 10. | Liquid paraffin | qs |
| 11. | Triisooctanoate glycerin | 15.0 |
| 12. | Sesqui-oleate sorbitan | 1.5 |
| 13. | Preservative | appropriate volume |
| 14. | Perfume | appropriate volume |

Production Process

The individual ingredients 1 to 8 were mixed together and ground together. To the resulting mixture was added a mixture of the individual ingredients 9 to 14. The resulting mixture was mixed together under agitation and molded in a mold, to prepare a solid foundation.

Example 11

Water-in-Oil Type Emulsified Foundation

| | | |
|---|---|---|
| 1. | Spherical nylon | 10.0 |
| 2. | Porous silicic anhydride powder | 8.0 |
| 3. | Titanium mica | 2.0 |
| 4. | Silicone-treated sericite | 2.0 |
| 5. | Silicone-treated mica | 12.0 |
| 6. | Silicone-treated titanium dioxide | 5.0 |
| 7. | Silicone-treated iron oxide | 2.0 |
| 8. | Ion exchange water | qs |
| 9. | 3-Hydroxy-5-piperidinopyridazine | 3.0 |
| 10. | Decamethylcyclopentane siloxane | 18.0 |
| 11. | Dimethylpolysiloxane | 5.0 |
| 12. | Squalene | 1.0 |
| 13. | Polyoxyethylene-modified dimethylpolysiloxane | 2.0 |
| 14. | Preservative | appropriate amount |
| 15. | Perfume | appropriate amount |

Production Process

The individual ingredients 9 to 15 were homogenously mixed together and dissolved, to which was added a ground mixture of the ingredients 1 to 7 to disperse the mixture therein. To the resulting dispersion was added the ingredient 8 for emulsification, which was then charged in a container to obtain a water-in-oil type emulsified foundation.

Example 12

Face Powder

| | | |
|---|---|---|
| 1. | Talc | qs |
| 2. | Sericite | 10.0 |
| 3. | Spherical nylon powder | 10.0 |
| 4. | Boron nitride | 5.0 |
| 5. | Iron oxide | 3.0 |
| 6. | Magnesium carbonate | 5.0 |
| 7. | Squalene | 3.0 |
| 8. | Triisooctanoate glycerin | 2.0 |
| 9. | Sesqui-oleate sorbitan | 2.0 |
| 10. | 3-Hydroxy-6-morpholinopyridazine | 0.1 |
| 11. | Preservative | appropriate amount |
| 12. | Perfume | appropriate amount |

Production Process

The individual ingredients 1 to 6 were mixed together and ground together. To the resulting mixture was added a mixture of the individual ingredients 7 to 12. The resulting mixture was mixed together under agitation, to prepare a face powder.

Example 13

Eye Shadow

| | | |
|---|---|---|
| 1. | Talc | qs |
| 2. | Mica | 15.0 |
| 3. | Spherical nylon powder | 10.0 |
| 4. | Boron nitride | 5.0 |
| 5. | Iron oxide | 3.0 |
| 6. | Titanium oxide-coated mica | 5.0 |
| 7. | Squalene | 3.0 |
| 8. | Triisooctanoate glycerin | 2.0 |
| 9. | Sesqui-oleate sorbitan | 2.0 |
| 10. | 3-Hydroxy-6-morpholinopyridazine | 2.0 |
| 11. | Preservative | appropriate amount |
| 12. | Perfume | appropriate amount |

Production Process

The individual ingredients 1 to 6 were mixed together and ground together. To the resulting mixture was added a mixture of the individual ingredients 7 to 12. The resulting mixture was mixed together under agitation, to prepare a face powder.

Example 14

Lipstick

| | | |
|---|---|---|
| 1. | Carnauba wax | 0.5 |
| 2. | Candelilla wax | 5.0 |
| 3. | Ceresin | 10.0 |
| 4. | Squalane | qs |
| 5. | Triisooctanoate glycerin | 10.0 |
| 6. | Diisostearate glycerin | 20.0 |
| 7. | 3,6-Dimorpholinopyridazine | 1.0 |
| 8. | Macadamia nut oil fatty acid cholesteryl | 4.0 |
| 9. | Synthetic sodium silicate-magnesium | 0.5 |
| 10. | Hydrophobic silica | 0.5 |
| 11. | Ion exchange water | 2.0 |
| 12. | Coloring agent | appropriate amount |
| 13. | Preservative | appropriate amount |
| 14. | Perfume | appropriate amount |

Production Process

The ingredient 8 was heated to 60°C., in which were dispersed the ingredients 9 and 10. To the resulting dispersion was added the ingredient 11 for sufficient agitation. Separately, the ingredients 1 to 7 were dissolved under heating, to which was added the resulting solution, for sufficient agitation. To the resulting solution were added the ingredients 12 to 14, for dispersion under agitation, which was then molded to prepare a lipstick.

All the makeup cosmetics of Examples 10 to 14 had excellent ultraviolet preventive effect, without any skin trouble or color change over time under observation.

Example 15

Hair Foam

| Formulation of Stock solution | |
|---|---|
| 1. Acrylic resin alkanol amine solution (50%) | 8.0 |
| 2. Polyoxyethylene-hydrogenated castor oil | appropriate amount |
| 3. Liquid paraffin | 5.0 |
| 4. Glycerin | 3.0 |
| 5. Perfume | appropriate amount |
| 6. Preservative | appropriate amount |
| 7. Ethanol | 15.0 |
| 8. 5-Bis(2-hydroxyethyl)amino-3-hydroxypyridazine | 0.01 |
| 9. Ion exchange water | qs |
| Formulation for charge | |
| 1. Stock solution | 90.0 |
| 2. Liquefied petroleum gas | 10.0 |

Production Process

Glycerin and polyoxyethylene-hydrogenated castor oil are dissolved together, to which is added liquid paraffin. The resulting mixture is homogenously emulsified with a homo-mixer. The emulsion is added to a solution of the remaining ingredients. As to charging, the stock solution is charged in a can, followed by valve arrangement to charge gas therein.

Example 16

Hair Liquid

| 1. Polyoxypropylene (40) butyl ether | 20.0 |
|---|---|
| 2. Polyoxyethylene-hydrogenated castor oil | 1.0 |
| 3. Ethanol | 50.0 |
| 4. Perfume | appropriate amount |
| 5. Preservative | appropriate amount |
| 6. Dye | appropriate amount |
| 7. 3,6-Bis(2-hydroxyethylamino)pyridazine | 2.0 |
| 8. Ion exchange water | qs |

Production Process

Polyoxypropylene (40) butyl ether, polyoxyethylene-hydrogenated castor oil, 3,6-bis(2-hydroxyethylamino) pyridazine, perfume and a preservative are dissolved in ethanol. A dye is dissolved in ion exchange water. The resulting aqueous phase is added to the ethanol phase, followed by filtration through a filter paper.

Example 17

Hair Spray

| 1. Acrylic resin alkanol amine solution (50%) | 7.0 |
|---|---|
| 2. Cetyl alcohol | 0.1 |
| 3. Silicone oil | 0.3 |
| 4. Ethanol | qs |
| 5. Perfume | appropriate amount |
| 6. 4,5-Dipiperidino-3-hydroxypyridazine | 2.0 |
| 7. Ion exchange water | 3.0 |
| Formulation for charge | |
| 1. Stock solution | 50.0 |
| 2. Liquefied petroleum gas | 50.0 |

Production Process

To ethanol are added the remaining ingredients, for dissolution and filtration. As to charging, the stock solution is charged in a can, followed by valve arrangement and gas charge.

Example 18

Hair Tonic

| 1. 3-Hydroxy-5-morpholinopyridazine | 3.0 |
|---|---|
| 2. Ethylene oxide (40 moles) adduct of Hydrogenated castor oil | 2.0 |
| 3. Ethanol | 60.0 |
| 4. Perfume | appropriate amount |
| 5. Ion exchange water | qs |

Production Process

In ethanol are dissolved an ethylene oxide (40 moles) adduct of hydrogenated castor oil and 3-hydroxy-5-morpholinopyridazine. The ethanol phase and the aqueous phase are mixed together, followed by addition of perfume.

All the hair and scalp cosmetics of Examples 15 to 18 had excellent ultraviolet prevent ion effect, without any scalp trouble or color change over time under observation.

The novel pyridazine derivative of the invention has very excellent ultraviolet absorption strongly absorbing ultraviolet ray over a wide wavelength range as an ultraviolet absorbent and also has a great photostabilization potency as a photostabilizer. Furthermore, the pyridazine derivative is highly safe and stable. Thus, external preparations for skin can be produced by blending the pyridazine derivative. The resulting external preparations for skin have high ultraviolet prevention effect and improved stability via the photostabilization effect.

What is claimed is:

1. An ultraviolet absorbent comprising as the effective ingredient the following pyridazine derivative:

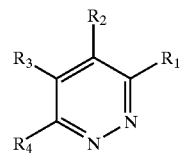

wherein $R_1$ and $R_4$ independently represent hydrogen atom, hydroxyl group, a lower alkyl group, a lower alkoxyl group or N $R_5$, $R_6$ group, wherein $R_5$ and $R_6$ may be the same or different and represent hydrogen atom, a lower alkyl group, or a lower hydroxyalkyl group or $R_5$ and $R_6$ taken together with nitrogen atom represent a heterocyclic group selected from the group consisting of aziridinyl group, azetidinyl group, pyrrolidinyl group, piperidino group, hexahydroazepinyl group, heptamethylene imino group, octamethylene imino group, morpholino group, thiomorpholino group, piperazinyl group, and 4-lower alkylpiperazinyl group; $R_2$ and $R_3$ independently represent hydrogen atom, bromine atom, chlorine atom, hydroxyl group, a lower alkyl group, a lower alkoxyl group, or $NR_7$, $R_8$ group, wherein $R_7$ and $R_8$ may be the same or different and represent hydrogen atom, a lower alkyl group, or a lower hydroxyalkyl group; or $R_7$ and $R_8$ taken together with nitrogen atom represent a heterocyclic group selected from the group consisting of aziridinyl group, azetidinyl group, pyrrolidinyl group, piperidino group, hexahydroazepinyl group, heptamethylene imino group, octamethylene imino group, morpholino group, thiomorpholino group, piperazinyl group, and 4-lower alkylpiperazinyl group; and wherein $R_1$, $R_2$, $R_3$ and $R_4$ are not simultaneously hydrogen atom and $R_2$ and $R_3$ are not simultaneously morpholino group; and a salt thereof.

2. An ultraviolet absorbent according to claim 1, where $R_1$ is hydroxyl group.

3. An ultraviolet absorbent according to claim 1, where $R_1$ is hydroxyl group and $R_4$ is hydrogen atom.

4. An ultraviolet absorbent according to claim 1, where $R_1$ represents hydroxyl group; $R_2$ and $R_3$ independently represent $NR_7$, $R_8$ group wherein $R_7$ and $R_8$ may be the same or different and represent hydrogen atom, a lower alkyl group, or a lower hydroxyalkyl group; or $R_7$ and $R_8$ taken together with nitrogen atom represent a heterocyclic group selected from the group consisting of aziridinyl group, azetidinyl group, pyrrolidinyl group, piperidino group, hexahydroazepinyl group, heptamethylene imino group, octamethylene imino group, morpholino group, thiomorpholino group, piperazinyl group, and 4-lower alkylpiperazinyl group, wherein $R_2$ and $R_3$ are not simultaneously morpholino group; and $R_4$ represents hydrogen atom.

5. An ultraviolet absorbent according to claim 1, where $R_1$ represents hydroxyl group; $R_2$ and $R_3$ independently represent N $R_7$, $R_8$ group wherein $R_7$ and $R_8$ may be the same or different and represent a lower hydroxyalkyl group or $R_7$ and $R_8$ taken together with nitrogen atom represent a heterocyclic group selected from the group consisting of pyrrolidinyl group, piperidino group, morpholino group, piperazinyl group, and 4-lower alkylpiperazinyl group, wherein $R_2$ and $R_3$ are not simultaneously morpholino group; and $R_4$ represents hydrogen atom.

6. A photostabilizer comprising one or both of a pyridazine derivative or a salt thereof according to claim 1.

7. An ultraviolet-absorbing composition comprising an ultraviolet absorbent according to claims 1.

8. A photostabilizer according to claim 6, which further contains a sequestering agent.

9. A photostabilizer composition, which comprises a photostabilizer according to claim 6.

10. An external preparation for skin, which contains an ultraviolet absorbent according to claim 1.

11. An external preparation for skin, which contains a photostabilizer according to claim 6.

12. An external preparation for skin according to claim 10, which additionally contains an inorganic powder.

13. An external preparation for skin according to claim 10, wherein the content of a pyridazine derivative or a salt thereof is 0.001 to 20 wt %.

14. A photostabilizer comprising one or both of a pyridazine derivative or a salt thereof according to claim 2.

15. A photostabilizer comprising one or both of a pyridazine derivative or a salt thereof according to claim 3.

16. A photostabilizer comprising one or both of a pyridazine derivative or a salt thereof according to claim 4.

17. A photostabilizer comprising one or both of a pyridazine derivative or a salt thereof according to claim 5.

18. An ultraviolet-absorbing composition comprising an ultraviolet absorbent according to claim 2.

19. An ultraviolet-absorbing composition comprising an ultraviolet absorbent according to claim 3.

20. An ultraviolet-absorbing composition comprising an ultraviolet absorbent according to claim 4.

21. An ultraviolet-absorbing composition comprising an ultraviolet absorbent according to claim 5.

22. A photostabilizer composition, which comprises a photostabilizer according to claim 8.

23. An external preparation for skin, which contains an ultraviolet absorbent according to claim 2.

24. An external preparation for skin, which contains an ultraviolet absorbent according to claim 3.

25. An external preparation for skin, which contains an ultraviolet absorbent according to claim 4.

26. An external preparation for skin, which contains an ultraviolet absorbent according to claim 5.

27. An external preparation for skin, which comprises an photostabilizer according to claim 8.

28. An external preparation for skin according to claim 11, wherein the content of a pyridazine derivative or a salt thereof is 0.001 to 20 wt %.

29. An external preparation for skin according to claim 12, wherein the content of a pyridazine derivative or a salt thereof is 0.001 to 20 wt %.

* * * * *

UNITED STATES PATENT AND TRADEMARK OFFICE
CERTIFICATE OF CORRECTION

PATENT NO.   : 6,676,932 B2
DATED        : January 13, 2004
INVENTOR(S)  : Masaru Suetsugu and Eijiro Hara It is certified that error appears in the above-identified patent and that said Letters Patent is hereby corrected as shown below:

Column 42,
Line 43, delete "N $R_5$, $R_6$" and substitute therefore -- N $R_5$ $R_6$ --
Line 54, delete "$NR_7$, $R_8$" and substitute therefore -- $NR_7$ $R_8$ --

Column 43,
Line 5, delete "$NR_7$, $R_8$" and substitute therefore -- $NR_7$ $R_8$ --
Line 18, delete "N $R_7$, $R_8$" and substitute therefore -- N $R_7$ $R_8$ --

Signed and Sealed this

Eleventh Day of May, 2004

JON W. DUDAS
*Acting Director of the United States Patent and Trademark Office*